United States Patent
Beier et al.

(10) Patent No.: US 8,580,799 B2
(45) Date of Patent: Nov. 12, 2013

(54) FUNGICIDE HYDROXIMOYL-HETEROCYCLES DERIVATIVES

(75) Inventors: Christian Beier, Saint Genis-Laval (FR); Jurgen Benting, Leichlingen (DE); David Bernier, Lyons (FR); Pierre-Yves Coqueron, Lyons (FR); Philippe Desbordes, Lyons (FR); Christophe Dubost, Lyons (FR); Stephanie Gary, Champagne au Mont d'Or (FR); Pierre Genix, Lyons (FR); Daniela Portz, Vettweiss (DE); Ulrike Wachendorff-Neumann, Neuwied (DE)

(73) Assignee: Bayer Cropscience AG (DE)

( * ) Notice: Subject to any disclaimer, the term of this patent is extended or adjusted under 35 U.S.C. 154(b) by 0 days.

(21) Appl. No.: 13/133,916

(22) PCT Filed: Dec. 8, 2009

(86) PCT No.: PCT/EP2009/066560
§ 371 (c)(1),
(2), (4) Date: Aug. 18, 2011

(87) PCT Pub. No.: WO2010/066697
PCT Pub. Date: Jun. 17, 2010

(65) Prior Publication Data
US 2011/0294829 A1   Dec. 1, 2011

(30) Foreign Application Priority Data

Dec. 9, 2008   (EP) .................................... 08356149

(51) Int. Cl.
*A01N 43/828*   (2006.01)
*A01N 43/832*   (2006.01)
*A01N 43/78*    (2006.01)
*C07D 417/14*   (2006.01)
*C07D 417/12*   (2006.01)
*C07D 413/12*   (2006.01)
*C07C 251/50*   (2006.01)

(52) U.S. Cl.
USPC .......... 514/256; 514/342; 514/361; 514/362; 514/339; 514/340; 514/370; 514/364; 514/365; 546/268.1; 546/268.7; 546/269.1; 544/328; 548/127; 548/134; 548/125; 548/197; 564/253; 564/256

(58) Field of Classification Search
USPC ................................ 546/268.1; 564/253, 256
See application file for complete search history.

(56) References Cited

U.S. PATENT DOCUMENTS 6,340,697 B1 *   1/2002   Kobori et al. ................. 514/364

FOREIGN PATENT DOCUMENTS

| EP | 0930305  | A | 7/1999 |
| EP | 1038874  | A | 9/2000 |
| EP | 1184382  | A | 3/2002 |
| EP | 1426371  | A | 6/2004 |
| JP | 2000351772 | A | 12/2000 |
| JP | 2002193713 | A | 7/2002 |

OTHER PUBLICATIONS

International Search Report issued Mar. 16, 2010 in corresponding International Application No. PCT/EP2009/066560.
Estela M.F. Muri, et al., "Synthesis of New Benzylic Ethers of Oximes Derived From 1-Phenyl-Pyrazole Compounds", Synthetic Communications, 28(7), pp. 1299-1321, (Jan. 1, 1998), XP009120673, ISSN: 0039-7911.

* cited by examiner

*Primary Examiner* — Yong Chu
(74) *Attorney, Agent, or Firm* — Ostrolenk Faber LLP

(57) ABSTRACT

The present invention relates to hydroximoyl-heterocycle derivatives of formula (I)

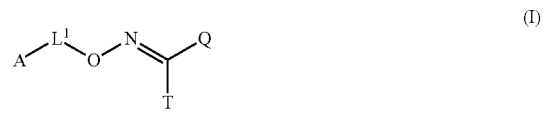

wherein T represents a substituted or non-substituted heterocyclyl group, Q represents a carbo or heterocyclic group, A represent a carbo or heterocyclic group or a carbo or heteropolycylic group, and L1 represents various linking groups, their process of preparation, intermediate compounds for their preparation, their use as fungicide active agents, particularly in the form of fungicide compositions, and methods for the control of phytopathogenic fungi, notably of plants, using these compounds or compositions.

12 Claims, No Drawings

FUNGICIDE HYDROXIMOYL-HETEROCYCLES DERIVATIVES

CROSS REFERENCE TO RELATED APPLICATION(S)

The present application is a 35 U.S.C. §371 national phase conversion of PCT/EP2009/066560 filed Dec. 8, 2009, which claims priority of European Application No. 08356149.8 filed Dec. 9, 2008. The PCT International Application was published in the English language.

The present invention relates to hydroximoyl-heterocycle derivatives, their process of preparation, their use as fungicide active agents, particularly in the form of fungicide compositions, and methods for the control of phytopathogenic fungi, notably of plants, using these compounds or compositions.

In European patent application n°1426371, there are disclosed certain tetrazoyloxime derivatives of the to following chemical structure:

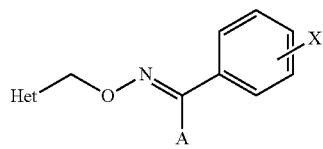

wherein A represents a tetrazolyl group, Het represents either a particular pyridinyl group or a particular thiazolyl group.

In Japanese patent application n°2004-131392, there are disclosed certain tetrazolyloxime derivatives of the following chemical structure:

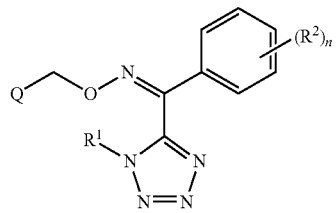

wherein Q can be selected in a list of 15 various heterocycle groups.

Nevertheless, the compounds disclosed in these two documents do not provide a comparable utility than the compounds according to the invention.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides hydroximoyl-heterocycle derivatives of formula (I)

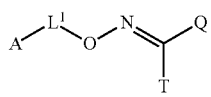

wherein
T represents a substituted or non-substituted heterocyclyl group that is selected in the list consisting of $T^1$ to $T^9$:

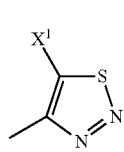

$T^1$

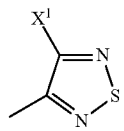

$T^2$

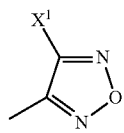

$T^3$

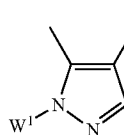

$T^4$

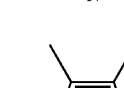

$T^5$

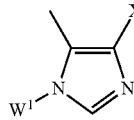

$T^6$

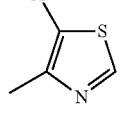

$T^7$

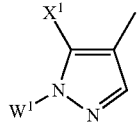

$T^8$

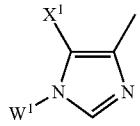

$T^9$ wherein
$X^1$ represents a hydrogen atom, a halogen atom, a nitro group, a hydroxy group, a cyano group, an amino group, a sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkykdi-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkylcarbamothioyl)-oxy, substituted or non-substituted substituted or non-substituted (di-$C_1$-$C_8$-alkylcarbamothioyl)-oxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)silyloxy or non-substituted $C_1$-$C_8$-alkylsulfenylamino, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms, substituted or non-substituted $C_1$-$C_8$-alkoxysulphonylamino, substituted or non-substituted $C_1$-$C_8$-halogenoxysulphonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, or a substituted or non-substituted (benzylideneamino)oxy;

$W^1$ represents a hydrogen atom, a formyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted aryl, or a substituted or non-substituted aryl-[$C_1$-$C_8$]-alkyl;

$L^1$ represents a direct bond or a divalent group selected in the list consisting of —$(CR^1R^2)_n$—  —$(CR^1R^2)_m$—C(=O)—$(CR^1R^2)_p$—
—$(CR^1R^2)_m$—$(CR^1=CR^2)$—$(CR^1R^2)_p$—
—$(CR^1R^2)_m$—C(=O)—O—$(CR^1R^2)_p$—
—$(CR^1R^2)_m$—C≡C—$(CR^1R^2)_p$—   —$(CR^1R^2)_m$—O—C(=O)—$(CR^1R^2)_p$—
—$(CR^1R^2)_m$—O—$(CR^1R^2)_p$—   —$(CR^1R^2)_m$—C(=O)—NH—$(CR^1R^2)_p$—
—$(CR^1R^2)_m$—NH—$(CR^1R^2)_p$—   —$(CR^1R^2)_m$—NH—C(=O)—$(CR^1R^2)_p$— wherein n represents 1, 2, 3 or 4;

m and p independently represent 0, 1, 2 or 3;

$R^1$ and $R^2$ independently represent a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, or a substituted or non-substituted $C_3$-$C_8$-halogenoalkynyloxy having 1 to 5 halogen atoms.

A is selected in the list consisting of $A^1$ to $A^{66}$:

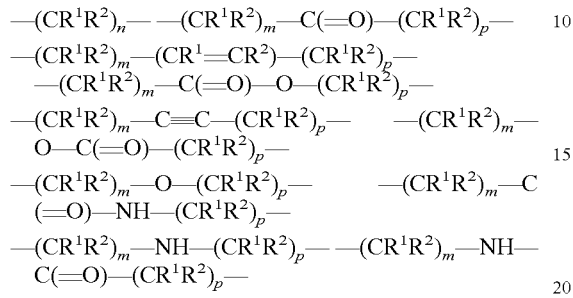

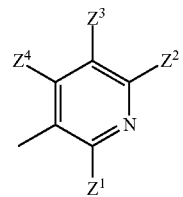

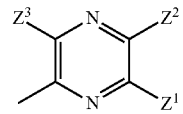

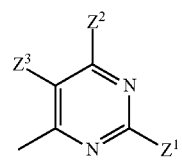

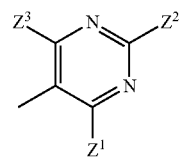

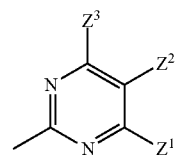

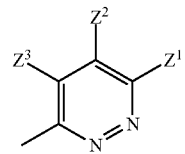

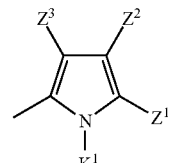

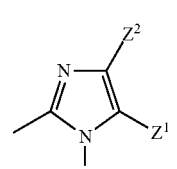

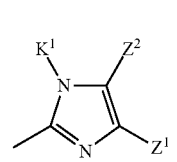

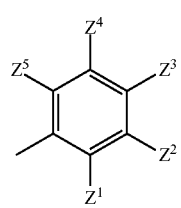

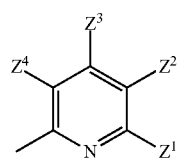

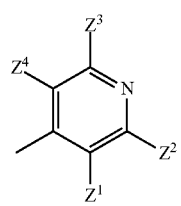

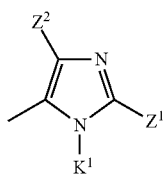
A13
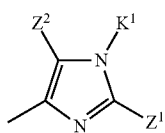
A14
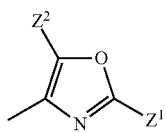
A15
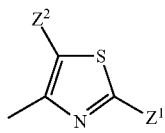
A16
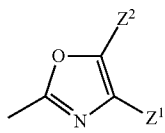
A17
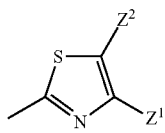
A18
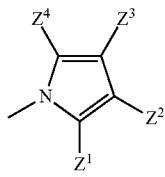
A19
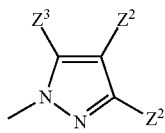
A20
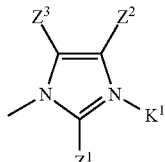
A21
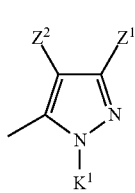
A22
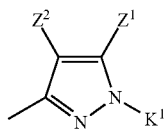
A23
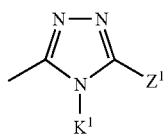
A24
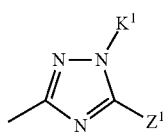
A25
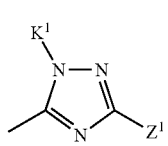
A26
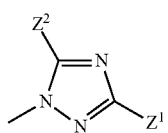
A27
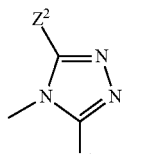
A28
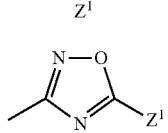
A29
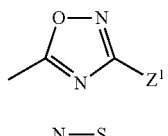
A30
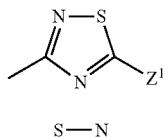
A31
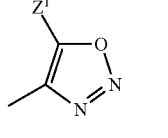
A32
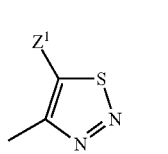
A33
A34

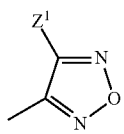
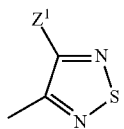
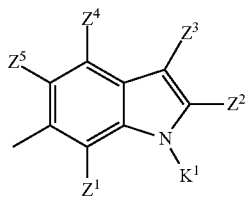
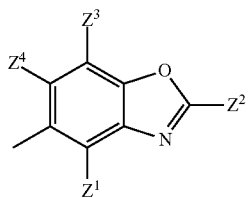
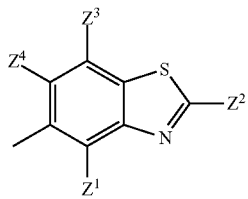
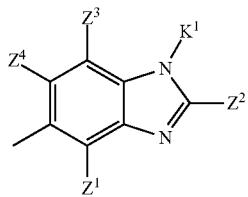
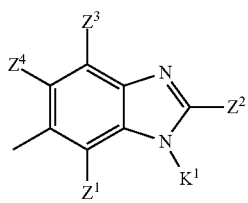
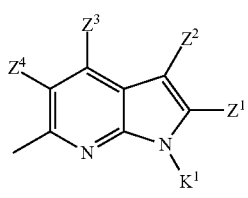
$A^{35}$
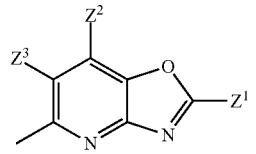
$A^{36}$
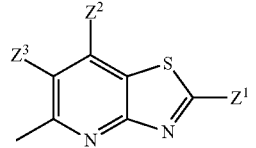
$A^{37}$
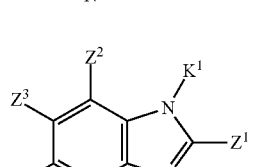
$A^{38}$
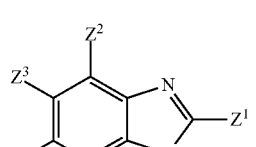
$A^{39}$
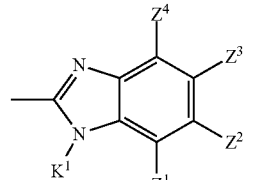
$A^{40}$
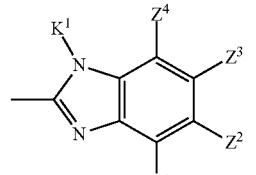
$A^{41}$
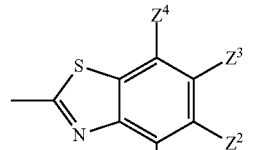
$A^{42}$
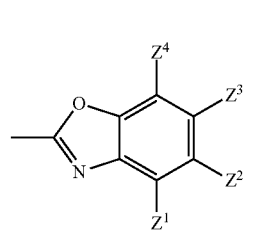
$A^{43}$
$A^{44}$
$A^{45}$
$A^{46}$
$A^{47}$
$A^{48}$
$A^{49}$
$A^{50}$ -continued
A⁵¹ 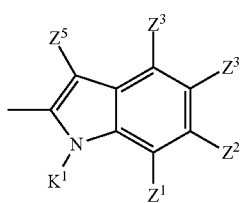
A⁵² 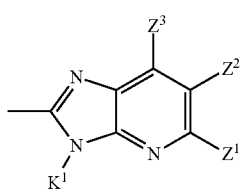
A⁵³ 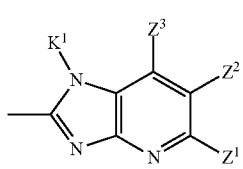
A⁵⁴ 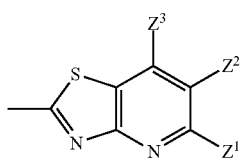
A⁵⁵ 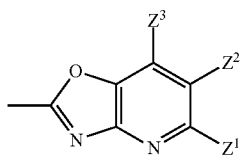
A⁵⁶ 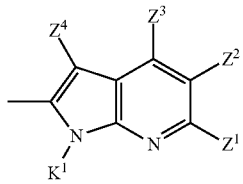
A⁵⁷ 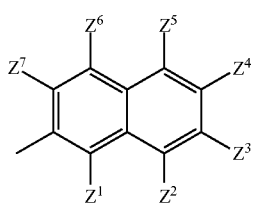
A⁵⁸ 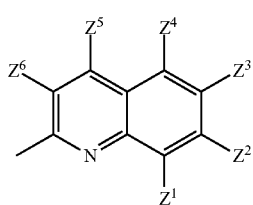
-continued
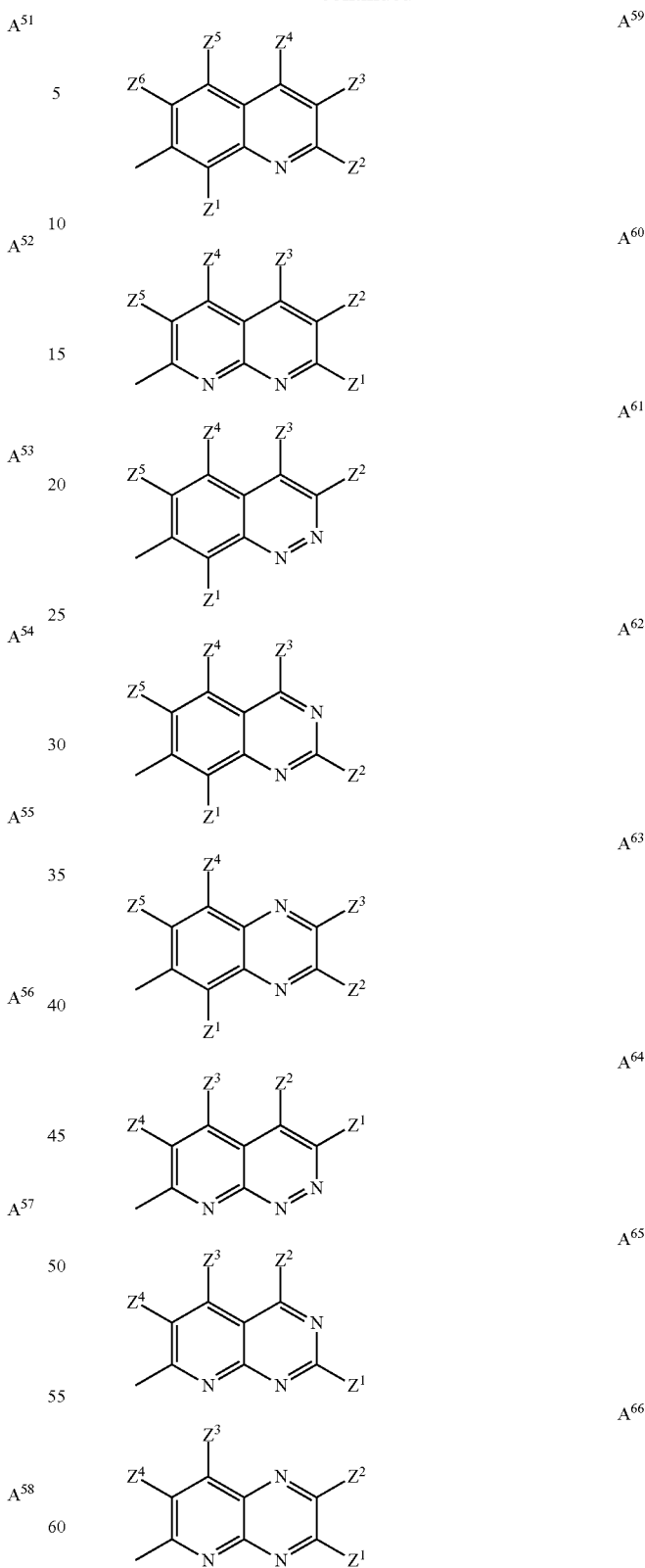
wherein
Z¹ represents a halogen atom, a nitro group, a hydroxy group, a cyano group, a sulphenyl group, a formyl group, a substituted or non-substituted carbaldehyde O—(C₁-

$C_8$-alkyl)oxime, a formyloxy group, a carbamoyl group, a N-hydroxycarbamoyl group, a pentafluoro-$\lambda^6$-sulphenyl group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted ($C_1$-$C_8$-alkoxycarbonyl)amino, substituted or non-substituted ($C_2$-$C_8$-alkenyloxycarbonyl)amino, substituted or non-substituted ($C_3$-$C_8$-alkynyloxycarbonyl)amino, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkykdi-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkoxythiocarbonyl)amino, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_8$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_8$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-alkylsulfenylamino, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms, substituted or non-substituted $C_1$-$C_8$-alkoxysulphonylamino, substituted or non-substituted $C_1$-$C_8$-halogenoxysulphonylamino having 1 to 5 halogen atoms, substituted or non-substituted tri($C_1$-$C_8$-alkyl)silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy, substituted or non-substituted [(arylcarbonyl)amino]-[$C_1$-$C_8$]-alkyl, substituted or non-substituted [{$C_1$-$C_8$-alkyl($C_1$-$C_8$-alkylcarbonyl)amino}]-[$C_1$-$C_8$]-alkyl, substituted or non-substituted [{$C_1$-$C_8$-alkyl(arylcarbonyl)amino}]-[$C_1$-$C_8$]-alkyl, substituted or non-substituted [($C_1$-$C_8$-alkylcarbonyl)amino]-[$C_1$-$C_8$]-alkyl;

$Z^2$, $Z^3$, $Z^4$, $Z^5$, $Z^6$ and $Z^7$ independently represent a hydrogen atom, a halogen atom, a nitro group, a hydroxy group, a cyano group, an amino group, a sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphenyl group, substituted or non-substituted $C_1$-$C_8$- alkoxyamino group, substituted or non-substituted N—C$_1$-C$_8$-alkyl-(C$_1$-C$_8$-alkoxy)-amino group, substituted or non-substituted (C$_1$-C$_8$-alkylamino)-amino group, substituted or non-substituted N—C$_1$-C$_8$-alkyl-(C$_1$-C$_8$-alkylamino)-amino group, a substituted or non-substituted (hydroxyimino)-C$_1$-C$_6$-alkyl group, substituted or non-substituted C$_1$-C$_8$-alkyl, substituted or non-substituted tri(C$_1$-C$_8$-alkyl)silyl-C$_1$-C$_8$-alkyl, substituted or non-substituted C$_1$-C$_8$-cycloalkyl, substituted or non-substituted tri(C$_1$-C$_8$-alkyl)silyl-C$_1$-C$_8$-cycloalkyl, substituted or non-substituted C$_1$-C$_8$-halogenoalkyl having 1 to 5 halogen atoms, substituted or non-substituted C$_1$-C$_8$-halogenocycloalkyl having 1 to 5 halogen atoms, a C$_2$-C$_8$-alkenyl, substituted or non-substituted C$_2$-C$_8$-alkynyl, substituted or non-substituted C$_1$-C$_8$-alkylamino, substituted or non-substituted di-C$_1$-C$_8$-alkylamino, substituted or non-substituted C$_1$-C$_8$-alkoxy, substituted or non-substituted (C$_1$-C$_8$-alkoxycarbonyl)amino, substituted or non-substituted (C$_2$-C$_8$-alkenyloxycarbonyl)amino, substituted or non-substituted (C$_3$-C$_8$-alkynyloxycarbonyl)amino, substituted or non-substituted C$_1$-C$_8$-halogenoalkoxy having 1 to 5 halogen atoms, substituted or non-substituted C$_1$-C$_8$-alkylsulphenyl, substituted or non-substituted C$_1$-C$_8$-halogenoalkylsulphenyl having 1 to 5 halogen atoms, substituted or non-substituted C$_2$-C$_8$-alkenyloxy, substituted or non-substituted C$_2$-C$_8$-halogenoalkenyloxy having 1 to 5 halogen atoms, substituted or non-substituted C$_3$-C$_8$-alkynyloxy, substituted or non-substituted C$_3$-C$_8$-halogenoalkynyloxy having 1 to 5 halogen atoms, substituted or non-substituted C$_1$-C$_8$-alkylcarbonyl, substituted or non-substituted N—(C$_1$-C$_8$-alkoxy)-C$_1$-C$_8$-alkanimidoyl, substituted or non-substituted N—(C$_1$-C$_8$-alkoxy)-C$_1$-C$_8$-halogenoalkanimidoyl having 1 to 5 halogen atoms, substituted or non-substituted C$_1$-C$_8$-halogenoalkylcarbonyl having 1 to 5 halogen atoms, substituted or non-substituted C$_1$-C$_8$-alkylcarbamoyl, substituted or non-substituted di-C$_1$-C$_8$-alkylcarbamoyl, substituted or non-substituted N—C$_1$-C$_8$-alkyloxycarbamoyl, substituted or non-substituted C$_1$-C$_8$-alkoxycarbamoyl, substituted or non-substituted N—C$_1$-C$_8$-alkyl-C$_1$-C$_8$-alkoxycarbamoyl, substituted or non-substituted C$_1$-C$_8$-alkoxycarbonyl, substituted or non-substituted C$_1$-C$_8$-halogenoalkoxycarbonyl having 1 to 5 halogen atoms, substituted or non-substituted C$_1$-C$_8$-alkylcarbonyloxy, substituted or non-substituted C$_1$-C$_8$-halogenoalkylcarbonyloxy having 1 to 5 halogen atoms, substituted or non-substituted C$_1$-C$_8$-alkylcarbonylamino, substituted or non-substituted C$_1$-C$_8$-halogenoalkylcarbonylamino having 1 to 5 halogen atoms, substituted or non-substituted C$_1$-C$_8$-alkylcarbamoylamino, substituted or non-substituted C$_1$-C$_8$-halogenoalkylcarbamoylamino having 1 to 5 halogen atoms, substituted or non-substituted di-C$_1$-C$_8$-alkylcarbamoylamino, substituted or non-substituted di-C$_1$-C$_8$-halogenoalkylcarbamoylamino having 1 to 5 halogen atoms, substituted or non-substituted N—C$_1$-C$_8$-alkyl-(C$_1$-C$_8$-alkylcarbamoyl)amino, substituted or non-substituted N—C$_1$-C$_8$-alkyl-(C$_1$-C$_8$-halogenoalkylcarbamoyl)amino having 1 to 5 halogen atoms, substituted or non-substituted N—C$_1$-C$_8$-alkyl-(di-C$_1$-C$_8$-alkylcarbamoyl)amino, substituted or non-substituted N—C$_1$-C$_8$-alkyl-(di-C$_1$-C$_8$-halogenoalkylcarbamoyl)amino having 1 to 5 halogen atoms, substituted or non-substituted C$_1$-C$_8$-alkylaminocarbonyloxy, substituted or non-substituted di-C$_1$-C$_8$-alkylaminocarbonyloxy, substituted or non-substituted C$_1$-C$_8$-alkylcarbamothioyl, substituted or non-substituted di-C$_1$-C$_8$-alkylcarbamothioyl, substituted or non-substituted N—C$_1$-C$_8$-alkyloxycarbamothioyl, substituted or non-substituted C$_1$-C$_8$-alkoxycarbamothioyl, substituted or non-substituted N—C$_1$-C$_8$-alkyl-C$_1$-C$_8$-alkoxycarbamothioyll, substituted or non-substituted C$_1$-C$_8$-alkylthioylamino, substituted or non-substituted C$_1$-C$_8$-halogenoalkylthioylamino having 1 to 5 halogen atoms, substituted or non-substituted (C$_1$-C$_8$-alkoxythiocarbonyl)amino, substituted or non-substituted (C$_1$-C$_8$-alkyl-carbamothioyl)-oxy, substituted or non-substituted substituted or non-substituted (di-C$_1$-C$_8$-alkyl-carbamothioyl)-oxy, substituted or non-substituted C$_1$-C$_8$-alkylsulphenyl, substituted or non-substituted C$_1$-C$_8$-halogenoalkylsulphenyl having 1 to 5 halogen atoms, substituted or non-substituted C$_1$-C$_8$-alkylsulphinyl, substituted or non-substituted C$_1$-C$_8$-halogenoalkylsulphinyl having 1 to 5 halogen atoms, substituted or non-substituted C$_1$-C$_8$-alkylsulphonyl, substituted or non-substituted C$_1$-C$_8$-halogenoalkylsulphonyl having 1 to 5 halogen atoms, substituted or non-substituted C$_1$-C$_8$-alkylaminosulfamoyl, substituted or non-substituted di-C$_1$-C$_8$-alkylaminosulfamoyl, substituted or non-substituted (C$_1$-C$_8$-alkoxyimino)-C$_1$-C$_6$-alkyl, substituted or non-substituted (C$_1$-C$_6$-alkenyloxyimino)-C$_1$-C$_6$-alkyl, substituted or non-substituted (C$_1$-C$_6$-alkynyloxyimino)-C$_1$-C$_6$-alkyl, substituted or non-substituted (benzyloxyimino)-C$_1$-C$_8$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[C$_1$-C$_8$]-alkyl, substituted or non-substituted tri(C$_1$-C$_8$-alkyl)-silyloxy, substituted or non-substituted C$_1$-C$_8$-alkylsulfenylamino, substituted or non-substituted C$_1$-C$_8$-halogenoalkylsulphinylamino having 1 to 5 halogen atoms, substituted or non-substituted C$_1$-C$_8$-alkylsulphonylamino, substituted or non-substituted C$_1$-C$_8$-halogenoalkylsulphonylamino having 1 to 5 halogen atoms, substituted or non-substituted C$_1$-C$_8$-alkoxysulphonylamino, substituted or non-substituted C$_1$-C$_8$-halogenoxysulphonylamino having 1 to 5 halogen atoms, substituted or non-substituted tri(C$_1$-C$_8$-alkyl)silyl, substituted or non-substituted (C$_1$-C$_8$-alkylideneamino)oxy, substituted or non-substituted (C$_1$-C$_6$-alkenylideneamino)oxy, substituted or non-substituted (C$_1$-C$_6$-alkynylideneamino)oxy, substituted or non-substituted (benzylideneamino)oxy, substituted or non-substituted [(arylcarbonyl)amino]-[C$_1$-C$_8$]-alkyl, substituted or non-substituted [{C$_1$-C$_8$-alkyl(C$_1$-C$_8$-alkylcarbonyl)amino}]-[C$_1$-C$_8$]-alkyl, substituted or non-substituted [{C$_1$-C$_8$-alkyl(arylcarbonyl)amino}]-[C$_1$-C$_8$]-alkyl, or a substituted or non-substituted [(C$_1$-C$_8$-alkylcarbonyl)amino]-[C$_1$-C$_8$]-alkyl;

Provided that when A represents A$^2$ to A$^9$, A$^{42}$ to A$^{46}$, A$^{58}$, A$^{60}$, A$^{64}$, A$^{65}$ or A$^{66}$, then Z$^1$, Z$^2$, Z$^3$, Z$^4$, Z$^5$, Z$^6$ and Z$^7$ independently cannot represent a hydrogen atom, a halogen atom, a cyano group, an amino group, a sulphenyl group, a formylamino group, substituted or non-substituted C$_1$-C$_8$-alkyl, substituted or non-substituted C$_1$-C$_8$-halogenoalkyl having 1 to 5 halogen atoms, substituted or non-substituted C$_1$-C$_8$-alkoxy, substituted or non-substituted C$_1$-C$_8$-halogenoalkoxy having 1 to 5 halogen atoms, substituted or non-substituted C$_1$-C$_8$-alkylsulphenyl, substituted or non-substituted C$_1$-C$_8$-halogenoalkylsulphenyl having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylsulphonyl, or a substituted or non-substituted $C_1$-$C_8$-halogenoalkylsulphonyl having 1 to 5 halogen atoms;

Provided that when A represents $A^{10}$ to $A^{36}$, $A^{47}$ to $A^{56}$, then $Z^1$, $Z^2$, $Z^3$, $Z^4$, $Z^5$, $Z^6$ and $Z^7$ independently cannot represent a hydrogen atom, a halogen atom, a cyano group, an amino group, a sulphenyl group, a formylamino group, a carbamoyl group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted ($C_1$-$C_8$-alkoxycarbonyl)amino, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted $C_1$-$C_8$-alkoxycarbonyl, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylsulphinyl, substituted or non-substituted $C_1$-$C_8$-alkylsulphonyl, substituted or non-substituted $C_1$-$C_8$-alkylaminosulfamoyl, substituted or non-substituted di-$C_1$-$C_8$-alkylaminosulfamoyl, substituted or non-substituted benzyloxy, substituted or non-substituted benzylsulphenyl, substituted or non-substituted benzylamino, or a substituted or non-substituted aryl;

$K^1$ represents a hydrogen atom, a formyl group, a carbamoyl group, a N-hydroxycarbamoyl group, a formylamino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkyl-sulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted aryl, substituted or non-substituted aryl-[$C_1$-$C_8$]-alkyl;

Q is selected in the list consisting of $Q^1$ to $Q^{19}$:

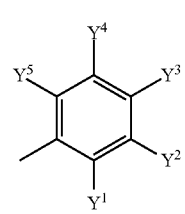

$Q^1$

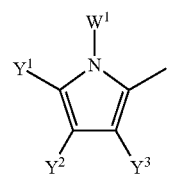

$Q^2$

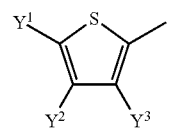

$Q^3$

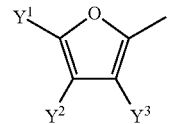

$Q^4$

-continued

Q⁵ 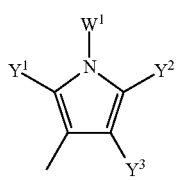

Q⁶ 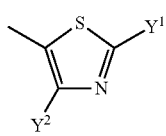

Q⁷ 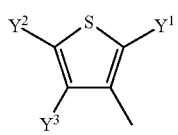

Q⁸ 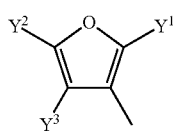

Q⁹ 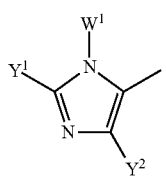

Q¹⁰ 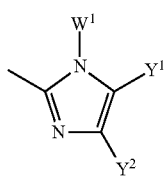

Q¹¹ 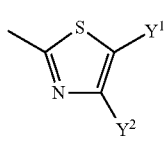

Q¹² 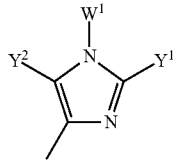

Q¹³ 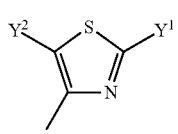

Q¹⁴ 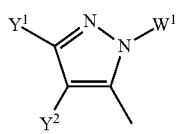

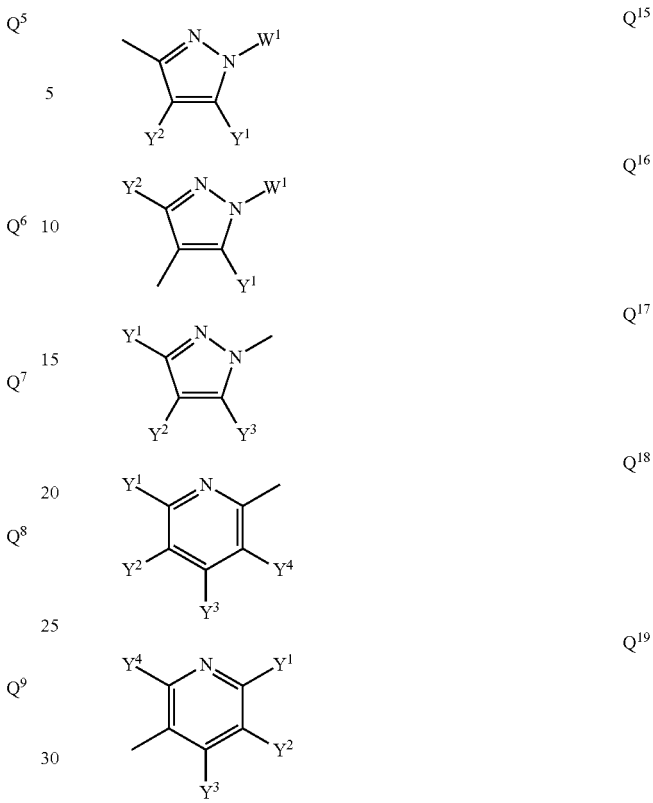

wherein
$Y^1$ to $Y^5$ independently represent a hydrogen atom, a nitro group, a hydroxy group, a cyano group, an amino group, a sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkykdi-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkylcarbamothioyl)-oxy, substituted or non-substituted substituted or non-substituted (di-$C_1$-$C_8$-alkylcarbamothioyl)-oxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxy)-$C_1$-$C_6$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)silyloxy, substituted or non-substituted $C_1$-$C_8$-alkylsulfenylamino, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms, substituted or non-substituted $C_1$-$C_8$-alkoxysulphonylamino, substituted or non-substituted $C_1$-$C_8$-halogenoxysulphonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, or a substituted or non-substituted (benzylideneamino)oxy;

$W^1$ represents a group as defined for T;

as well as salts, N-oxides, metallic complexes and metalloidic complexes thereof or (E) and (Z) isomers and mixtures thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

Notably, the stereostructure of the oxime moiety present in the heterocyclyloxime derivative of formula (I) includes (E) or (Z) isomer, and these stereoisomers form part of the present invention.

According to the invention, the following generic terms are generally used with the following meanings:

halogen means fluorine, chlorine, bromine or iodine;

heteroatom can be nitrogen, oxygen or sulphur;

unless indicated otherwise, a group or a substituent that is substituted according to the invention can be substituted by one or more of the following groups or atoms: a halogen atom, a nitro group, a hydroxy group, a cyano group, an amino group, a sulphenyl group, a pentafluoro-$\lambda^6$-sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a formylamino group, a (hydroxyimino)-$C_1$-$C_6$-alkyl group, a $C_1$-$C_8$-alkyl, a tri($C_1$-$C_8$-alkyl)silyl-$C_1$-$C_8$-alkyl, $C_1$-$C_8$-cycloalkyl, tri($C_1$-$C_8$-alkyl)silyl-$C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulphenyl, a $C_1$-$C_8$-halogenoalkylsulphenyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_8$-alkylaminosulfamoyl, a di-$C_1$-$C_8$-alkylaminosulfamoyl, a ($C_1$-$C_6$-alkoxyimino)-$C_1$-$C_6$-alkyl, a ($C_1$-$C_8$-alkenyloxyimino)-$C_1$-$C_8$-alkyl, a ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, benzyloxy, benzylsulphenyl, benzylamino, phenoxy, phenylsulphenyl, or phenylamino;

the term "aryl" means phenyl or naphthyl.

The term "heterocyclyl" means saturated or unsaturated 4-, 5-, 6- or 7-membered heterocyclyl comprising up to 4 heteroatoms selected in the list consisting of N, O, S Preferred compounds of formula (I) according to the invention are those wherein $L^1$ represents a direct bond or a divalent group selected in the list consisting of —$(CR^1R^2)_n$— —$C(=O)$—$(CR^1R^2)_p$—
—$(CR^1R^2)_m$—O— —$(CR^1R^2)_m$—$C(=O)$—O—
—$(CR^1R^2)_m$—NH— —$(CR^1R^2)_m$—$C(=O)$—NH—
—$(CR^1R^2)_m$—$C(=O)$— —$(CR^1R^2)_m$—NH—$C(=O)$ wherein n represents 1 or 2;

m and p independently represent 0 or 1;

$R^1$ and $R^2$ independently represent a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms.

More preferred compounds of formula (I) according to the invention are those wherein $L^1$ represents a direct bond or a divalent group selected in the list consisting of —$(CR^1R^2)$—, —$C(=O)$—$(CR^1R^2)$— and —$C(=O)$—; wherein $R^1$ and $R^2$ are independently selected in the list consisting of hydrogen, halogen, methyl, ethyl, isopropyl, trifluoromethyl, difluoromethyl, allyl, ethynyl, propargyl, cyclopropyl, methoxy, trifluoromethoxy and cyano.

Other preferred compounds of formula (I) according to the invention are those wherein T represents $T^2$ or $T^3$.

Other preferred compounds of formula (I) according to the invention are those wherein $X^1$ represents a hydrogen atom, a halogen atom, a cyano group, an amino group, a sulphenyl group, a pentafluoro-$\lambda^6$-sulphenyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_8$-alkynyloxyimino)-$C_1$-$C_8$-alkyl, substituted or non-substituted (benzyloxyimino)-$C_1$-$C_6$-alkyl, substituted or non-substituted benzyloxy, substituted or non-substituted benzylsulphenyl, substituted or non-substituted phenoxy, substituted or non-substituted phenylsulphenyl, substituted or non-substituted aryl, substituted or non-substituted aryl-[$C_1$-$C_8$]-alkyl, substituted or non-substituted tri($C_1$-$C_8$-alkyl)-silyloxy, or a substituted or non-substituted tri($C_1$-$C_8$-alkyl)-silyl.

Other more preferred compounds of formula (I) according to the invention are those wherein $X^1$ represents a hydrogen atom, a halogen atom, methyl, isopropyl, isobutyl, tertbutyl, trifluoromethyl, difluoromethyl, allyl, ethynyl, propargyl, cyclopropyl, benzyl, phenethyl, methoxy, trifluoromethoxy, acetyl, trifluoroacetyl or cyano.

Other preferred compounds of formula (I) according to the invention are those wherein $W^1$ represents a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted phenoxy, substituted or non-substituted aryl, or a substituted or non-substituted aryl-[$C_1$-$C_8$]-alkyl. Other more preferred compounds of formula (I) according to the invention are those wherein $W^1$ represents a hydrogen atom, a halogen atom, methyl, ethyl, isopropyl, isobutyl, terbutyl, trifluoromethyl, difluoromethyl, allyl, ethynyl, propargyl, cyclopropyl, methoxy, trifluoromethoxy or cyano.

Other preferred compounds of formula (I) according to the invention are those wherein A is selected in the list consisting of $A^2$ to $A^{18}$.

Other more preferred compounds of formula (I) according to the invention are those wherein A is selected in the list consisting of $A^2$, $A^8$, $A^{16}$ and $A^{18}$.

Other preferred compounds of formula (I) according to the invention are those wherein $Z^1$ represents a halogen atom, an amino group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted $C_1$-$C_8$-alkyl, substituted or non-substituted $C_1$-$C_8$-cycloalkyl, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-alkylcarbonyl, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted ($C_1$-$C_8$-alkoxycarbonyl)amino, substituted or non-substituted ($C_2$-$C_8$-alkenyloxycarbonyl)amino, substituted or non-substituted ($C_3$-$C_8$-alkynyloxycarbonyl)amino, substituted or non-substituted $C_1$-$C_8$-alkylcarbamoylamino, substituted or non-substituted ($C_1$-$C_8$-alkoxythiocarbonyl)amino, substituted or non-substituted di-$C_1$-$C_8$-alkylcarbamoylamino, substituted or non-substituted $C_1$-$C_8$-alkylthioylamino, substituted or non-substituted benzylamino, substituted or non-substituted phenylamino, substituted or non-substituted aryl-[$C_1$-$C_8$]-alkyl.

More preferred compounds of formula (I) according to the invention are those wherein $Z^1$ represents an amino group, a formylamino group, substituted or non-substituted $C_1$-$C_8$-alkoxyamino group, substituted or non-substituted $C_1$-$C_8$-alkyl, substituted or non-substituted $C_1$-$C_8$-cycloalkyl, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted ($C_1$-$C_8$-alkoxycarbonyl)amino, substituted or non-substituted ($C_2$-$C_8$-alkenyloxycarbonyl)amino, substituted or non-substituted ($C_3$-$C_8$-alkynyloxycarbonyl)amino, substituted or non-substituted ($C_1$-$C_8$-alkoxythiocarbonyl)amino, substituted or non-substituted di-$C_1$-$C_8$-alkylcarbamoylamino, substituted or non-substituted $C_1$-$C_8$-alkylthioylamino, substituted or non-substituted benzylamino, substituted or non-substituted phenylamino, substituted or non-substituted aryl-[$C_1$-$C_8$]-alkyl.

Other preferred compounds of formula (I) according to the invention are those wherein $Z^2$ to $Z^9$ independently represent a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted phenoxy, substituted or non-substituted aryl, or a substituted or non-substituted aryl-[$C_1$-$C_8$]-alkyl.

Other more preferred compounds of formula (I) according to the invention are those wherein $Z^2$ to $Z^9$ are independently selected in the list consisting of hydrogen, halogen, methyl, ethyl, isopropyl, isobutyl, terbutyl, trifluoromethyl, difluoromethyl, allyl, ethynyl, propargyl, cyclopropyl, methoxy, trifluoromethoxy, acetyl, and cyano.

Other preferred compounds of formula (I) according to the invention are those wherein $K^1$ is selected in the list consisting of hydrogen, methyl, ethyl, isopropyl, isobutyl, terbutyl, allyl, propargyl, cyclopropyl, acetyl, trifluoroacetyl and mesyl.

Other preferred compounds of formula (I) according to the invention are those wherein Q is selected in the list consisting of $Q^1$, $Q^3$, $Q^7$.

Other more preferred compounds of formula (I) according to the invention are those wherein Q represents $Q^1$.

Other preferred compounds of formula (I) according to the invention are those wherein $Y^1$ to $Y^5$ independently represent a hydrogen atom, a halogen atom, a cyano group, an amino group, a sulphenyl group, a pentafluoro-$\lambda^6$-sulphenyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted ($C_1$-$C_6$-alkoxyimino)-$C_1$-$C_6$-alkyl, substituted or non-substituted (C₁-C₆-alkenyloxyimino)-C₁-C₆-alkyl, substituted or non-substituted (C₁-C₈-alkynyloxyimino)-C₁-C₈-alkyl, substituted or non-substituted (benzyloxyimino)-C₁-C₆-alkyl, substituted or non-substituted benzyloxy, substituted or non-substituted benzylsulphenyl, substituted or non-substituted phenoxy, substituted or non-substituted phenylsulphenyl, substituted or non-substituted aryl, substituted or non-substituted aryl-[C₁-C₈]-alkyl, substituted or non-substituted tri(C₁-C₈-alkyl)silyloxy, substituted or non-substituted tri(C₁-C₈-alkyl)silyl.

Other more preferred compounds of formula (I) according to the invention are those wherein Y¹ to Y⁵ independently represent a hydrogen atom, a halogen atom, methyl, isopropyl, isobutyl, tertbutyl, trifluoromethyl, difluoromethyl, allyl, ethynyl, propargyl, cyclopropyl, methoxy, trifluoromethoxy or cyano.

The above mentioned preferences with regard to the substituents of the compounds of formula (I) according to the invention can be combined in various manners. These combinations of preferred features thus provide sub-classes of compounds according to the invention. Examples of such sub-classes of preferred compounds according to the invention can combine:

preferred features of A with preferred features of one or more of L¹, T and Q;
preferred features of L¹ with preferred features of one or more of A, T and Q;
preferred features T with preferred features of one or more of A, L¹ and Q;
preferred features of Q with preferred features of one or more of A, L¹ and T.

In these combinations of preferred features of the substituents of the compounds according to the invention, the said preferred features can also be selected among the more preferred features of each of A, L¹, T and Q, so as to form most preferred subclasses of compounds according to the invention.

The preferred features of the other substituents of the compounds according to the invention can also be part of such sub-classes of preferred compounds according to the invention, notably the groups of substituents X¹ to X⁶, n, m, R¹, R², Z¹ to Z⁷, K¹, Y¹ to Y⁵ and W¹.

The present invention also relates to a process for the preparation of compounds of formula (I), Thus, according to a further aspect of the present invention, there is provided a process P1 for the preparation of compounds of formula (I) as herein-defined, as illustrated by the following reaction schemes.

non-substituted C₁-C₈-alkylamino, substituted or non-substituted C₁-C₈-halogenoalkylamino having 1 to 5 halogen atoms, a formylamino group, substituted or non-substituted C₁-C₈-alkoxyamino group, substituted or non-substituted N—C₁-C₈-alkyl-(C₁-C₈-alkoxy)-amino group, substituted or non-substituted (C₁-C₈-alkylamino)-amino group, substituted or non-substituted N—C₁-C₈-alkyl-(C₁-C₈-alkylamino)-amino group, substituted or non-substituted C₁-C₈-alkylcarbonylamino, substituted or non-substituted C₁-C₈-halogenoalkylcarbonylamino having 1 to 5 halogen atoms, substituted or non-substituted C₁-C₈-alkoxycarbonylamino, substituted or non-substituted C₁-C₈-halogenoalkoxycarbonylamino having 1 to 5 halogen atoms, substituted or non-substituted C₁-C₈-alkylcarbamoylamino, substituted or non-substituted C₁-C₈-halogenoalkylcarbamoylamino having 1 to 5 halogen atoms, substituted or non-substituted di-C₁-C₈-alkylcarbamoylamino, substituted or non-substituted C₁-C₈-alkylthioylamino, substituted or non-substituted C₁-C₈-halogenoalkylthioylamino having 1 to 5 halogen atoms, substituted or non-substituted (C₁-C₈-alkyl-carbamothioyl)-amino, substituted or non-substituted (di-C₁-C₈-alkyl-carbamothioyl)-amino, process P1 according to the invention can be completed by a further step comprising the additional modification of this group, notably by a reaction of alkylation, acylation, alkoxycarbonylation, alkylaminocarbonylation and alkylaminothiocarbonylation, to yield to a compound of formula (Ib), according to known methods. In such a case there is provided a process P2 according to the invention and such a process P2 can be illustrated by the following reaction schemes:

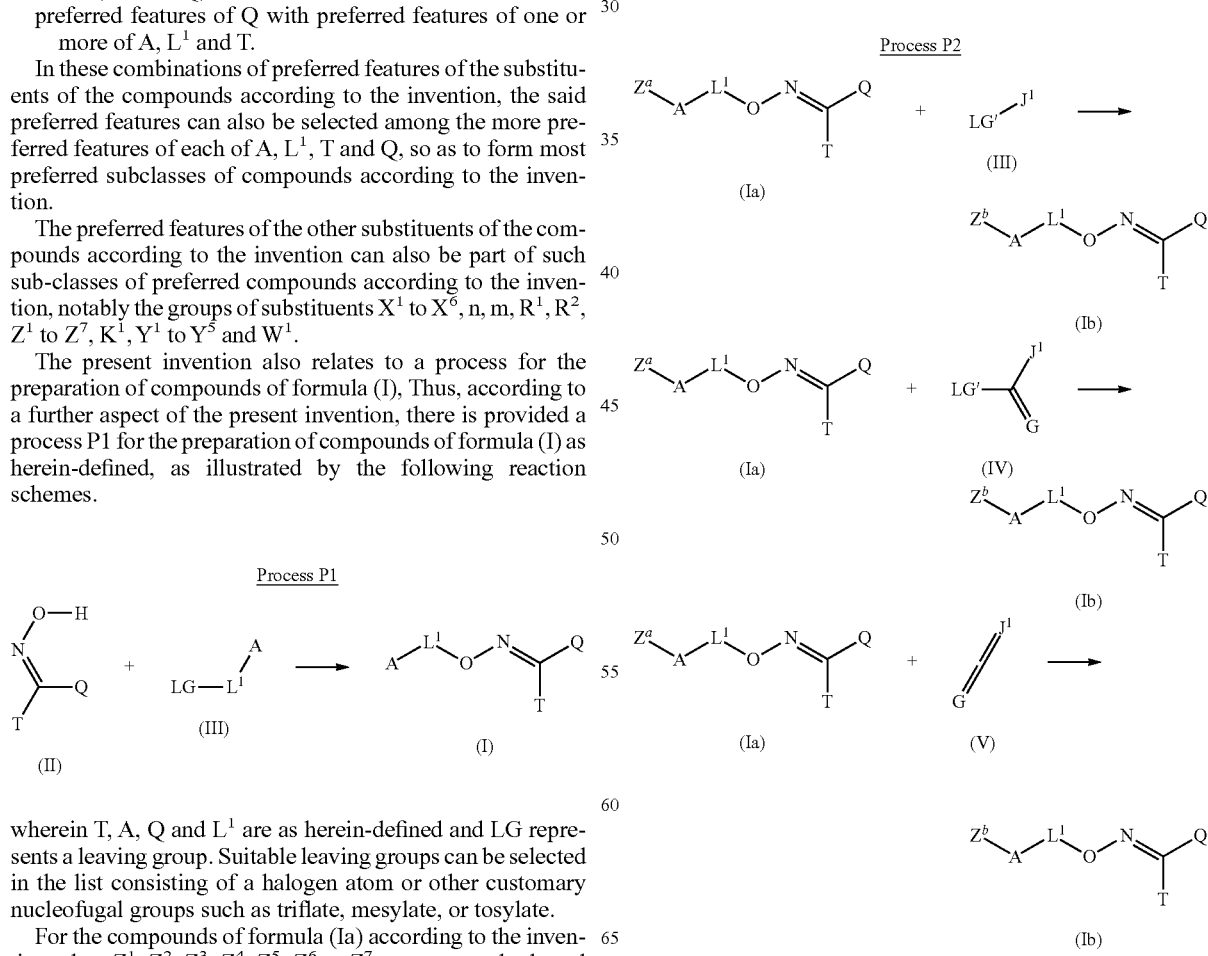

wherein T, A, Q and L¹ are as herein-defined and LG represents a leaving group. Suitable leaving groups can be selected in the list consisting of a halogen atom or other customary nucleofugal groups such as triflate, mesylate, or tosylate.

For the compounds of formula (Ia) according to the invention when Z¹, Z², Z³, Z⁴, Z⁵, Z⁶ or Z⁷ represents a hydroxyl group, a sulphenyl group, an amino group, substituted or wherein
- T, A, Q and $L^1$ are as herein-defined, LG' represents a leaving group, $J^1$ optionally represents a hydrogen atom, a formyl group, substituted or non-substituted $C_1$-$C_8$-alkyl, substituted or non-substituted $C_1$-$C_8$-halogenoalkyl having 1 to 5 halogen atoms, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms;
- $Z^a$ represents a hydroxyl group, a sulphenyl group, an amino group, substituted or non-substituted $C_1$-$C_8$-alkylamino, substituted or non-substituted $C_1$-$C_8$-halogenoalkylamino having 1 to 5 halogen atoms, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-amino, substituted or non-substituted (di-$C_1$-$C_8$-alkyl-carbamothioyl)-amino,
- G represents an oxygen atom or a sulphur atom;
- $Z^b$ represents a formyloxy group, a formylamino group, a formylamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkoxycarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted ($C_1$-$C_8$-alkyl-carbamothioyl)-amino, substituted or non-substituted substituted or non-substituted (di-$C_1$-$C_8$-alkylcarbamothioyl)-amino, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted benzyloxy, substituted or non-substituted benzylsulphenyl, substituted or non-substituted benzylamino, substituted or non-substituted tri($C_1$-$C_8$-alkyl)-silyloxy.

Suitable leaving groups can be selected in the list consisting of a halogen atom or other customary nucleofugal groups such as alcoolate, hydroxide or cyanide.

For the compounds of formula (Ic) according to the invention when $Z^1$, $Z^2$, $Z^3$, $Z^4$, $Z^5$, $Z^6$ or $Z^7$ represent a substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkylcarbamothioyl)-oxy, substituted or non-substituted substituted or non-substituted (di-$C_1$-$C_8$-alkylcarbamothioyl)-oxy, substituted or non-substituted ($C_1$-$C_8$-alkyl-carbamothioyl)-amino, substituted or non-substituted substituted or non-substituted (di-$C_1$-$C_8$-alkyl-carbamothioyl)-amino, process P1 according to the invention can be completed by a further step comprising the additional modification of this group, notably by a reaction of thiocarbonylation in the presence of a thiocarbonylating agent such as 2,4-bis(4-methoxyphenyl)-1,3,2,4-dithiadiphosphetane 2,4-disulfide, phosphorus pentasulfide, sulphur to yield to a compound of formula (Id), according to known methods. In such a case there is provided a process P3 according to the invention and such a process P3 can be illustrated by the following reaction scheme:

Process P3

$$Z^c\diagdown A\diagup L^1\diagdown O\diagup N=\underset{T}{\overset{}{C}}-Q \longrightarrow$$

(Ic)

-continued

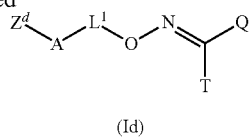

(Id)

wherein

T, A, Q and $L^1$ are as herein-defined, $Z^c$ represents a substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted ($C_1$-$C_8$-alkyl-carbamoyl)-oxy, substituted or non-substituted substituted or non-substituted (di-$C_1$-$C_8$-alkyl-carbamoyl)-oxy, substituted or non-substituted ($C_1$-$C_8$-alkyl-carbamoyl)-amino, substituted or non-substituted substituted or non-substituted (di-$C_1$-$C_8$-alkyl-carbamoyl)-amino, And $Z^d$ represents a substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted ($C_1$-$C_8$-alkyl-carbamothioyl)-amino, substituted or non-substituted substituted or non-substituted (di-$C_1$-$C_8$-alkyl-carbamothioyl)-amino.

For the compounds of formula (Ie) according to the invention when $Z^1$, $Z^2$, $Z^3$, $Z^4$, $Z^5$, $Z^6$ or $Z^7$ represent a hydroxy group, a cyano group, an amino group, a sulphenyl group, a formyloxy group, a formylamino group, a carbamoyl group, a N-hydroxycarbamoyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, process P1 according to the invention can be completed by a further step comprising the additional modification of this group, notably by a reaction of nucleophilic substitution to yield to a compound of formula (If), according to known methods, optionally in the presence of carbon monoxide or a carbon monoxide generating agent such as $Mo(CO)_6$ or $W(CO)_6$, optionally in the presence of a catalyst notably a transition metal catalyst, such as palladium salts or complexes for example palladium (II) chloride, palladium (II) acetate, tetrakis(triphenylphosphine) palladium(0), bis-(triphenylphosphine) palladium dichloride (II), tris(dibenzylideneacetone) dipalladium(0), bis(dibenzylideneacetone) palladium(0), or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl]ethyldicyclohexylphosphine, (R)-(−)-1-[(S)-2-(diphenylphosphino)ferrocenyl]ethyldicyclohexylphosphine, (S)-(+)-1-[(R)-2-(diphenylphosphino)ferrocenyl]ethyldi-t-butylphosphine, optionally in the presence of a base such as an inorganic or an organic base; preferably an alkaline earth metal or alkali metal hydride, hydroxide, amide, alcoholate, acetate, carbonate or hydrogen carbonate, such as sodium hydride, sodium amide, lithium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amine, such as trimethylamine, triethylamine (TEA), tributylamine, N,N-dimethylaniline, N,N-dimethylbenzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), to yield a compound of formula (I). In such a case there is provided a process P4 according to the invention and such a process P4 can be illustrated by the following reaction scheme:

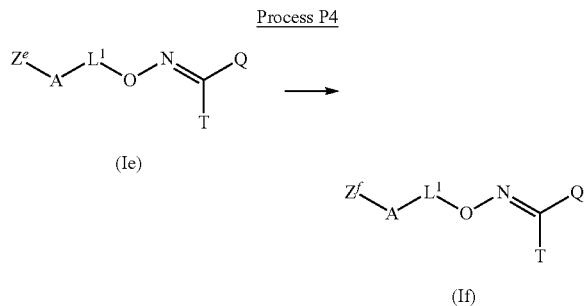

wherein
T, A, Q and $L^1$ are as herein-defined as herein-defined, $Z^e$ represents a halogen atom, and $Z^f$ represents a hydroxy group, a cyano group, an amino group, a sulphenyl group, a formyloxy group, a formylamino group, a carbamoyl group, a N-hydroxycarbamoyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, If $Z^1$, $Z^2$, $Z^3$, $Z^4$, $Z^5$, $Z^6$ or $Z^7$ represent a protected amino group, carrying out process P2 would previously require a deprotection step in order to yield the amino group. Amino-protecting groups and related methods of cleavage thereof are known and can be found in T. W. Greene and P. G. M. Wuts, *Protective Group in Organic Chemistry*, $3^{rd}$ ed., John Wiley & Sons.

According to the invention, processes P1 and P2 may be performed if appropriate in the presence of a solvent and if appropriate in the presence of a base.

According to the invention, processes P1 and P2 may be performed if appropriate in the presence of a catalyst. Suitable catalyst may be chosen as being 4-dimethyl-aminopyridine, 1-hydroxy-benzotriazole or dimethylformamide.

In case LG' represents a hydroxy group, the process P2 according to the present invention may be performed in the presence of condensing agent. Suitable condensing agent may be chosen as being acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromo-tripyrrolidino-phosphonium-hexafluorophosphate.

Suitable solvents for carrying out processes P1 to P4 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

Suitable bases for carrying out processes P1 and P2 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

When carrying out processes P1 and P4 according to the invention, the reaction temperature can independently be varied within a relatively wide range. Generally, process P1 according to the invention is carried out at temperatures between −80° C. and 160° C.

Processes P1 to P4 according to the invention are generally independently carried out under atmospheric pressure. However, it is also possible to operate under elevated or reduced pressure.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that may still be present.

Compounds according to the invention can be prepared according to the above described processes. It will to nevertheless be understood that, on the basis of his general knowledge and of available publications, the skilled worker will be able to adapt these processes according to the specifics of each of the compounds according to the invention that is desired to be synthesised.

When T represents a compound of formula $T^2$ to $T^9$ as described previously, the compounds of formula (II), useful as a starting material, can be prepared, for example, by reacting hydroxylamine with the corresponding ketones that can be prepared, for example, according to the method described in WO99/02689.

In a further aspect, the present invention relates to compounds of formula (II) useful as intermediate compounds or materials for the process of preparation according to the invention. The present invention thus provides compounds of formula (II) wherein T and Q are as herein-defined:

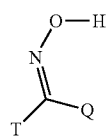

(II)

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic organic or inorganic compound with which the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols and derivatives of the above compounds containing sulphate, sulphonate and phosphate functions. The presence of at least one surfactant is generally essential if the active compound and/or the inert support are water-insoluble and if the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity. The mixtures with other fungicide compounds are particularly advantageous. The composition according to the invention comprising a mixture of a compound of formula (I) with a bactericide compound can also be particularly advantageous Examples of suitable fungicide mixing partners can be selected in the following lists:

(1) Inhibitors of the nucleic acid synthesis, for example benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.

(2) Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide and 5-chloro-7-(4-methylpiperidin-1-yl)-6-(2,4,6-trifluorophenyl)[1,2,4]triazolo[1,5-a]pyrimidine.

(3) inhibitors of the respiratory chain at complex I or II, for example diflumetorim as CI-respiration inhibitor;

bixafen, boscalid, carboxin, diflumetorim, fenfuram, fluopyram, flutolanil, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-(3',4',5'-trifluorobiphenyl-2-yl)-1H-pyrazole-4-carboxamide, 3-(difluoromethyl)-1-methyl-N-[2-(1,1,2,2-tetrafluoroethoxy)phenyl]-1H-pyrazole-4-carboxamide and 3-(difluoromethyl)-N-[4-fluoro-2-(1,1,2,3,3,3-hexafluoropropoxy)phenyl]-1-methyl-1H-pyrazole-4-carboxamide CII-respiration inhibitor;

amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl 2-{2-[({cyclopropyl[(4-methoxyphenyl)imino]methyl}sulfanyl)methyl]phenyl}-3-methoxyacrylate and N-(3-ethyl-3,5,5-trimethylcyclohexyl)-3-(formylamino)-2-hydroxybenzamide as CIII-respiration inhibitor.

(4) Compounds capable to act as an uncoupler, like for example binapacryl, dinocap, ferimzone, fluazinam and meptyldinocap.

(5) Inhibitors of the ATP production, for example fentin acetate, fentin chloride, fentin hydroxide and silthiofam.

(6) Inhibitors of the amino acid and/or protein biosynthesis, for example andoprim, blasticidin-S, cyprodinil, kasugamycin, kasugamycin hydrochloride hydrate, mepanipyrim and pyrimethanil.

(7) Inhibitors of the signal transduction, for example chlozolinate, fenpiclonil, fludioxonil, iprodione, procymidone, quinoxyfen and vinclozolin.

(8) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(9) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-{1-[(4-methoxyphenoxy)methyl]-2,2-dimethylpropyl}1H-imidazole-1-carbothioate,

(10) Inhibitors of the cell wall synthesis, for example benthiavalicarb, dimethomorph, flumorph, iprovalicarb, mandipropamid, polyoxins, polyoxorim, validamycin A and valifenalate.

(11) Inhibitors of the melanine biosynthesis, for example carpropamid, diclocymet, fenoxanil, phthalide, pyroquilon and tricyclazole,

(12) Compounds capable to induce a host defence, like for example acibenzolar-5-methyl, isotianil, probenazole and tiadinil.

(13) Compounds capable to have a multisite action, like for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.

(14) Further compounds like for example 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-[(4-methoxyphenoxy)methyl]-2,2-dimethylpropyl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-butoxy-6-iodo-3-propyl-4H-chromen-4-one, 2-phenylphenol and salts, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-prop-2-yn-1-ylthiophene-2-sulfonohydrazide, 5-methyl-6-octyl-3,7-dihydro[1,2,4]triazolo[1,5-a]pyrimidin-7-amine, ametoctradin, benthiazole, bethoxazin, capsimycin, carvone, chinomethionat, chlazafenone, cufraneb, cyflufenamid, cymoxanil, cyprosulfamide, dazomet, debacarb, dichlorophen, diclomezine, difenzoquat, difenzoquat methylsulphate, diphenylamine, ecomate, ethyl (2Z)-3-amino-2-cyano-3-phenylprop-2-enoate, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mild iomycin, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, natamycin, nickel dimethyldithiocarbamate, nitrothal-isopropyl, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, octhilinone, oxamocarb, oxyfenthiin, pentachlorophenol and salts, pentyl {6-[({[(1-methyl-1H-tetrazol-5-yl)(phenyl)methylidene]amino}oxy)methyl]pyridin-2-yl}carbamate, phenazine-1-carboxylic acid, phenothrin, phosphorous acid and its salts, propamocarb-fosetylate, propanosine-sodium, proquinazid, pyrrolnitrine, quinolin-8-ol, quinolin-8-ol sulfate (2:1) (salt), fenpyrazamine, tebufloquin, tecloftalam, tolnifanide, triazoxide, trichlamide and zarilamid.

According to another object of the present invention, there is provided a method for controlling the phytopathogenic fungi of plants, crops or seeds, characterized in that an agronomically effective and substantially non-phytotoxic quantity of a pesticide composition according to the invention is applied as seed treatment, foliar application, stem application, drench or drip application (chemigation) to the seed, the plant or to the fruit of the plant or to soil or to inert substrate (e.g. inorganic substrates like sand, rockwool, to glasswool; expanded minerals like perlite, vermiculite, zeolite or expanded clay), Pumice, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to grow. The expression "are applied to the plants to be treated" is understood to mean, for the purposes of the present invention, that the pesticide composition which is the subject of the invention can be applied by means of various methods of treatment such as:

spraying onto the aerial parts of the said plants a liquid comprising one of the said compositions, dusting, the incorporation into the soil of granules or powders, spraying, around the said plants and in the case of trees injection or daubing, coating or film-coating the seeds of the said plants with the aid of a plant-protection mixture comprising one of the said compositions.

The method according to the invention can either be a curing, preventing or eradicating method.

In this method, a composition used can be prepared beforehand by mixing the two or more active compounds according to the invention.

According to an alternative of such a method, it is also possible to apply simultaneously, successively or separately compounds (A) and (B) so as to have the conjugated (A)/(B) effects, of distinct compositions each containing one of the two or three active ingredients (A) or (B).

The dose of active compound usually applied in the method of treatment according to the invention is generally and advantageously for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;

for seed treatment: from 2 to 200 g per 100 kilogram of seed, preferably from 3 to 150 g per 100 kilogram of seed;

for soil treatment: from 0.1 to 10,000 g/ha, preferably from 1 to 5,000 g/ha.

The doses herein indicated are given as illustrative Examples of method according to the invention. A person skilled in the art will know how to adapt the application doses, notably according to the nature of the plant or crop to be treated.

Under specific conditions, for example according to the nature of the phytopathogenic fungus to be treated or controlled, a lower dose can offer adequate protection. Certain climatic conditions, resistance or other factors like the nature of the phytopathogenic fungi or the degree of infestation, for example, of the plants with these fungi, can require higher doses of combined active ingredients. The optimum dose usually depends on several factors, for example on the type of phytopathogenic fungus to be treated, on the type or level of development of the infested plant, on the density of vegetation or alternatively on the method of application. Without it being limiting, the crop treated with the pesticide composition or combination according to the invention is, for example, grapevine, but this could be cereals, vegetables, lucerne, soybean, market garden crops, turf, wood, tree or horticultural plants.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

Among the plants that can be protected by the method according to the invention, mention can be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

The composition according to the invention can also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties or genes for improving the agronomic quality of the modified plant.

The composition according to the invention can also be used against fungal diseases liable to grow on or inside timber. The term "timber" means all types of species of wood and all types of working of this wood intended for construction, for example solid wood, high-density wood, laminated wood and plywood. The method for treating timber according to the invention mainly consists in contacting one or more compounds according to the invention or a composition according to the invention; this includes for example direct application, spraying, dipping, injection or any other suitable means.

Among the diseases of plants or crops that can be controlled by the method according to the invention, mention can be made of:

Powdery mildew diseases such as:
Blumeria diseases, caused for example by *Blumeria graminis*;
Podosphaera diseases, caused for example by *Podosphaera leucotricha*;
Sphaerotheca diseases, caused for example by *Sphaerotheca fuliginea*;
Uncinula diseases, caused for example by *Uncinula necator*;
Rust diseases such as:
Gymnosporangium diseases, caused for example by *Gymnosporangium sabinae*;
Hemileia diseases, caused for example by *Hemileia vastatrix*;
Phakopsora diseases, caused for example by *Phakopsora pachyrhizi* or *Phakopsora meibomiae*;
Puccinia diseases, caused for example by *Puccinia recondite, Puccinia graminis* or *Puccinia striiformis*;
Uromyces diseases, caused for example by *Uromyces appendiculatus*;
Oomycete diseases such as:
Albugo diseases caused for example by *Albugo candida*;
Bremia diseases, caused for example by *Bremia lactucae*;
Peronospora diseases, caused for example by *Peronospora pisi* or *P. brassicae*;
Phytophthora diseases, caused for example by *Phytophthora infestans*;
Plasmopara diseases, caused for example by *Plasmopara viticola*;
Pseudoperonospora diseases, caused for example by *Pseudoperonospora humuli* or *Pseudoperonospora cubensis*;
Pythium diseases, caused for example by *Pythium ultimum*;
Leafspot, leaf blotch and leaf blight diseases such as:
Alternaria diseases, caused for example by *Alternaria solani*;
Cercospora diseases, caused for example by *Cercospora beticola*;
Cladiosporum diseases, caused for example by *Cladiosporium cucumerinum*;
Cochliobolus diseases, caused for example by *Cochliobolus sativus* (Conidiaform: Drechslera, Syn: Helminthosporium) or *Cochliobolus miyabeanus*;
Colletotrichum diseases, caused for example by *Colletotrichum lindemuthanium*;
Cycloconium diseases, caused for example by *Cycloconium oleaginum*;
Diaporthe diseases, caused for example by *Diaporthe citri*;
Elsinoe diseases, caused for example by *Elsinoe fawcettii*;
Gloeosporium diseases, caused for example by *Gloeosporium laeticolor*;
Glomerella diseases, caused for example by *Glomerella cingulata*;
Guignardia diseases, caused for example by *Guignardia bidwelli*;
Leptosphaeria diseases, caused for example by *Leptosphaetia maculans; Leptosphaeria nodorum*;
Magnaporthe diseases, caused for example by *Magnaporthe grisea*;
Mycosphaerella diseases, caused for example by *Mycosphaerella graminicola*; Mycosphaerella arachidicola; *Mycosphaerella fijiensis*;
Phaeosphaeria diseases, caused for example by *Phaeosphaeria nodorum*;
Pyrenophora diseases, caused for example by *Pyrenophora teres*, or *Pyrenophora tritici repentis*;
Ramularia diseases, caused for example by *Ramularia cofio-cygni*, or *Ramularia areola*;
Rhynchosporium diseases, caused for example by *Rhynchosporium secalis*;
Septoria diseases, caused for example by *Septoria apii* or *Septoria lycopercisi*;
Typhula diseases, caused for example by *Typhula incamata*;
Venturia diseases, caused for example by *Venturia inaequalis*;
Root, Sheath and stem diseases such as:
Corticium diseases, caused for example by *Corticium graminearum*;
Fusarium diseases, caused for example by *Fusarium oxysporum*;

Gaeumannomyces diseases, caused for example by *Gaeumannomyces graminis*;
Rhizoctonia diseases, caused for example by *Rhizoctonia solani*;
Sarocladium diseases caused for example by *Sarocladium oryzae*;
Sclerotium diseases caused for example by *Sclerotium oryzae*;
Tapesia diseases, caused for example by *Tapesia acuformis*;
Thielaviopsis diseases, caused for example by *Thielaviopsis basicola*;
Ear and panicle diseases such as:
Alternaria diseases, caused for example by *Alternaria* spp.;
Aspergillus diseases, caused for example by *Aspergillus flavus*;
Cladosporium diseases, caused for example by *Cladosporium* spp.;
Claviceps diseases, caused for example by *Claviceps purpurea*;
Fusarium diseases, caused for example by *Fusarium culmorum*;
Gibberella diseases, caused for example by *Gibberella zeae*;
Monographella diseases, caused for example by *Monographella nivalis*;
Smut and bunt diseases such as:
Sphacelotheca diseases, caused for example by *Sphacelotheca reiliana*;
Tilletia diseases, caused for example by *Tilletia caries*;
Urocystis diseases, caused for example by *Urocystis occulta*;
Ustilago diseases, caused for example by *Ustilago nuda*;
Fruit rot and mould diseases such as:
Aspergillus diseases, caused for example by *Aspergillus flavus*;
Botrytis diseases, caused for example by *Botrytis cinerea*;
Penicillium diseases, caused for example by *Penicillium expansum*;
Rhizopus diseases caused by example by *Rhizopus stolonifer*
Sclerotinia diseases, caused for example by *Sclerotinia sclerotiorum*;
Verticilium diseases, caused for example by *Verticilium alboatrum*;
Seed and soilborne decay, mould, wilt, rot and damping-off diseases:
Alternaria diseases, caused for example by *Alternaria brassicicola*
Aphanomyces diseases, caused for example by *Aphanomyces euteiches*
Ascochyta diseases, caused for example by *Ascochyta lentis*
Aspergillus diseases, caused for example by *Aspergillus flavus*
Cladosporium diseases, caused for example by *Cladosporium herbarum*
Cochliobolus diseases, caused for example by *Cochliobolus sativus* (Conidiaform: *Drechslera*, *Bipolaris* Syn: *Helminthosporium*);
Colletotrichum diseases, caused for example by *Colletotrichum coccodes*;
Fusarium diseases, caused for example by *Fusarium culmorum*;
Gibberella diseases, caused for example by *Gibberella zeae*;
Macrophomina diseases, caused for example by *Macrophomina phaseolina*
Monographella diseases, caused for example by *Monographella nivalis*;
Penicillium diseases, caused for example by *Penicillium expansum*
Phoma diseases, caused for example by *Phoma lingam*
Phomopsis diseases, caused for example by *Phomopsis sojae*;
Phytophthora diseases, caused for example by Phytophthora cactorum;
Pyrenophora diseases, caused for example by *Pyrenophora graminea*
Pyricularia diseases, caused for example by *Pyricularia oryzae*;
Pythium diseases, caused for example by *Pythium ultimum*;
Rhizoctonia diseases, caused for example by *Rhizoctonia solani*;
Rhizopus diseases, caused for example by *Rhizopus oryzae*
Sclerotium diseases, caused for example by *Sclerotium rolfsii*;
Septoria diseases, caused for example by *Septoria nodorum*;
Typhula diseases, caused for example by *Typhula incarnata*;
Verticillium diseases, caused for example by *Verticillium dahliae*;
Canker, broom and dieback diseases such as:
Nectria diseases, caused for example by *Nectria geffigena*;
Blight diseases such as:
Monilinia diseases, caused for example by *Monilinia laxa*;
Leaf blister or leaf curl diseases such as:
Exobasidium diseases caused for example by *Exobasidium vexans*
Taphrina diseases, caused for example by *Taphrina deformans*;
Decline diseases of wooden plants such as:
Esca diseases, caused for example by *Phaemoniella clamydospora*;
Eutypa dyeback, caused for example by *Eutypa lata*;
Ganoderma diseases caused for example by *Ganoderma boninense*;
Rigidoporus diseases caused for example by *Rigidoporus lignosus*
Diseases of Flowers and Seeds such as
Botrytis diseases caused for example by *Botrytis cinerea*;
Diseases of Tubers such as
Rhizoctonia diseases caused for example by *Rhizoctonia solani*;
Helminthosporium diseases caused for example by *Helminthosporium solani*;
Club root diseases such as
Plasmodiophora diseases, cause for example by *Plamodiophora brassicae*.
Diseases caused by Bacterial Organisms such as
Xanthomonas species for example *Xanthomonas campestris* pv. oryzae;
Pseudomonas species for example *Pseudomonas syringae* pv. lachrymans;
Erwinia species for example *Erwinia amylovora*.

The compounds according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The various aspects of the invention will now be illustrated with reference to the following table I of compound examples and the following preparation or efficacy examples.

The following table illustrates in a non-limiting manner examples of compounds according to the invention. In the following table, M+H (or M−H) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

TABLE I (I)

In Table I we use the following abbreviations for specified moieties A and T in formula (I):

A²_1, A⁸_1, A¹⁶_1

T¹, T², T³, T⁴_1

| Example | A | Z¹ | L¹ | Q | T | X¹ or W¹ (T⁴_1) | MW | logp |
|---|---|---|---|---|---|---|---|---|
| 1 | A²_1 | hexylamino | CH₂ | 3-fluorophenyl | T¹ | CH₃ | 428 | 3.06[b] |
| 2 | A²_1 | hexylamino | CH₂ | 3-chlorophenyl | T¹ | CH₃ | 444 | 3.27[b] |
| 3 | A²_1 | hexylamino | CH₂ | 4-fluorophenyl | T¹ | CH₃ | 428 | 2.9[b] |
| 4 | A¹⁶_1 | hex-1-yn-1-yl | CH₂ | 4-chlorophenyl | T¹ | CH₃ | 431 | 5.68[b] |
| 5 | A¹⁶_1 | hex-1-yn-1-yl | CH₂ | 4-fluorophenyl | T¹ | CH₃ | 415 | 5.19[b] |
| 6 | A¹⁶_1 | hex-1-yn-1-yl | CH₂ | 3-chlorophenyl | T¹ | CH₃ | 431 | 5.68[b] |
| 7 | A¹⁶_1 | hex-1-yn-1-yl | CH₂ | 3-fluorophenyl | T¹ | CH₃ | 415 | 5.25[b] |
| 8 | A⁸_1 | amino | CH₂ | phenyl | T² | CF₃ | 381 | 1.75[a] |
| 9 | A⁸_1 | [(pentyloxy)carbonyl]amino | CH₂ | phenyl | T² | CF₃ | 495 | 4.92[a] |
| 10 | A¹⁶_1 | amino | CH₂ | phenyl | T² | CF₃ | 386 | 2.26[a] |
| 11 | A⁸_1 | (phenylcarbonyl)amino | CH₂ | phenyl | T² | CF₃ | 485 | 4.14[a] |
| 12 | A⁸_1 | (4-phenylbutanoyl)amino | CH₂ | phenyl | T² | CF₃ | 527 | 4.65[a] |
| 13 | A⁸_1 | [(2-methoxyethoxy)acetyl]amino | CH₂ | phenyl | T² | CF₃ | 497 | 3.46[a] |
| 14 | A⁸_1 | (3-methylbutanoyl)amino | CH₂ | phenyl | T² | CF₃ | 465 | 4.09[a] |
| 15 | A⁸_1 | (phenylacetyl)amino | CH₂ | phenyl | T² | CF₃ | 499 | 4.09[a] |
| 16 | A⁸_1 | (2,2-dimethylpropanoyl)amino | CH₂ | phenyl | T² | CF₃ | 465 | 4.24[a] |
| 17 | A⁸_1 | hexanoylamino | CH₂ | phenyl | T² | CF₃ | 479 | 4.54[a] |
| 18 | A²_1 | 1,3-dioxo-1,3-dihydro-2H-isoindol-2-yl | CH₂ | phenyl | T² | CF₃ | 510 | 4.31[a] |
| 19 | A²_1 | [(pentyloxy)carbonyl]amino | CH₂ | phenyl | T² | CF₃ | 494 | 5.68[a] |
| 20 | A²_1 | [(pentyloxy)carbonyl]amino | CH₂ | phenyl | T² | CH₃ | 440 | 5.5[b] |
| 21 | A²_1 | [(cyclopentyloxy)carbonyl]amino | CH₂ | phenyl | T² | CH₃ | 438 | 5.11[b] |
| 22 | A²_1 | [(benzyloxy)carbonyl]amino | CH₂ | phenyl | T² | CH₃ | 460 | 4.92[b] |
| 23 | A²_1 | [(hexyloxy)carbonyl]amino | CH₂ | phenyl | T² | CH₃ | 454 | 5.99[b] |
| 24 | A²_1 | [(but-3-en-1-yloxy)carbonyl]amino | CH₂ | phenyl | T² | CH₃ | 424 | 4.65[b] |
| 25 | A²_1 | [(but-2-yn-1-yloxy)carbonyl]amino | CH₂ | phenyl | T² | CH₃ | 422 | 4.28[b] |
| 26 | A²_1 | [(heptyloxy)carbonyl]amino | CH₂ | phenyl | T² | CH₃ | 468 | 6.42[b] |
| 27 | A²_1 | {[(2-ethylhexyl)oxy]carbonyl}amino | CH₂ | phenyl | T² | CH₃ | 482 | 6.76[b] |
| 28 | A²_1 | {[(5,5,5-trifluoropentyl)oxy]carbonyl}amino | CH₂ | phenyl | T² | CH₃ | 494 | 4.97[b] |
| 29 | A²_1 | bis(tert-butoxycarbonyl)amino | CH₂ | phenyl | T² | CH₃ | 526 | 5.47[b] |
| 30 | A²_1 | (tert-butoxycarbonyl)amino | CH₂ | phenyl | T² | CH₃ | 426 | 4.97[b] |
| 31 | A²_1 | hexylamino | CH₂ | phenyl | T² | CH₃ | 410 | 3.11[b] |
| 32 | A²_1 | butylamino | CH₂ | phenyl | T² | CH₃ | 382 | 2.41[b] |
| 33 | A²_1 | ethylamino | CH₂ | phenyl | T² | CH₃ | 354 | 1.89[b] |
| 34 | A²_1 | propylamino | CH₂ | phenyl | T² | CH₃ | 368 | 2.11[b] |
| 35 | A²_1 | hex-5-en-1-ylamino | CH₂ | phenyl | T² | CH₃ | 408 | 2.78[b] |
| 36 | A²_1 | (3-phenylpropyl)amino | CH₂ | phenyl | T² | CH₃ | 444 | 2.98[b] |
| 37 | A²_1 | (2-cyclohexylethyl)amino | CH₂ | phenyl | T² | CH₃ | 436 | 3.46[b] |
| 38 | A²_1 | pentylamino | CH₂ | phenyl | T² | CH₃ | 396 | 2.7[b] |
| 39 | A²_1 | hexylamino | CH₂ | phenyl | T² | CF₃ | 464 | 3.44[b] |
| 40 | A¹⁶_1 | hex-1-yn-1-yl | CH₂ | phenyl | T² | CF₃ | 451 | 6.37[b] |
| 41 | A¹⁶_1 | hex-1-yn-1-yl | CH₂ | phenyl | T² | CH₃ | 397 | 5.72[b] |

TABLE I-continued

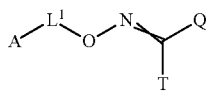

(I)

| | | | | | | | | | |
|---|---|---|---|---|---|---|---|---|---|
| 42 | $A^2\_1$ | hexylamino | $CH_2$ | 3-fluorophenyl | $T^3$ | $CH_3$ | 412 | $3.57^{[b]}$ |
| 43 | $A^2\_1$ | hexylamino | $CH_2$ | phenyl | $T^3$ | $CH_3$ | 394 | $3.31^{[b]}$ |
| 44 | $A^{16}\_1$ | hex-1-yn-1-yl | $CH_2$ | 4-fluorophenyl | $T^3$ | $CH_3$ | 399 | $5.99^{[b]}$ |
| 45 | $A^{16}\_1$ | hex-1-yn-1-yl | $CH_2$ | phenyl | $T^3$ | $CH_3$ | 381 | $5.51^{[b]}$ |
| 46 | $A^{16}\_1$ | hex-1-yn-1-yl | $CH_2$ | 3-fluorophenyl | $T^3$ | $CH_3$ | 399 | $5.59^{[b]}$ |
| 47 | $A^{16}\_1$ | hex-1-yn-1-yl | $CH_2$ | 2-fluorophenyl | $T^3$ | $CH_3$ | 399 | $5.39^{[b]}$ |
| 48 | $A^{16}\_1$ | amino | $CH_2$ | phenyl | $T^4\_1$ | $CH_3$ | 314 | $1.5^{[b]}$ |
| 49 | $A^{16}\_1$ | bromo | $CH_2$ | phenyl | $T^4\_1$ | $CH_3$ | 378 | $3.39^{[b]}$ |
| 50 | $A^{16}\_1$ | (phenoxyacetyl)amino | $CH_2$ | phenyl | $T^4\_1$ | $CH_3$ | 448 | $3.55^{[b]}$ |
| 51 | $A^{16}\_1$ | (3-phenylpropanoyl)amino | $CH_2$ | phenyl | $T^4\_1$ | $CH_3$ | 446 | $3.69^{[b]}$ |
| 52 | $A^{16}\_1$ | hexanoylamino | $CH_2$ | phenyl | $T^4\_1$ | $CH_3$ | 412 | $3.8^{[b]}$ |
| 53 | $A^{16}\_1$ | (phenylacetyl)amino | $CH_2$ | phenyl | $T^4\_1$ | $CH_3$ | 432 | $3.42^{[b]}$ |
| 54 | $A^{16}\_1$ | (2,2-dimethylpropanoyl)amino | $CH_2$ | phenyl | $T^4\_1$ | $CH_3$ | 398 | $3.46^{[b]}$ |
| 55 | $A^{16}\_1$ | pentanoylamino | $CH_2$ | phenyl | $T^4\_1$ | $CH_3$ | 398 | $3.39^{[b]}$ |
| 56 | $A^{16}\_1$ | heptanoylamino | $CH_2$ | phenyl | $T^4\_1$ | $CH_3$ | 426 | $4.18^{[b]}$ |
| 57 | $A^{16}\_1$ | [(4-chlorobutoxy)carbonyl]amino | $CH_2$ | phenyl | $T^4\_1$ | $CH_3$ | 448 | $3.65^{[b]}$ |
| 58 | $A^{16}\_1$ | (butoxycarbonyl)amino | $CH_2$ | phenyl | $T^4\_1$ | $CH_3$ | 414 | $3.76^{[b]}$ |
| 59 | $A^{16}\_1$ | [(hexyloxy)carbonyl]amino | $CH_2$ | phenyl | $T^4\_1$ | $CH_3$ | 442 | $4.59^{[b]}$ |
| 60 | $A^{16}\_1$ | [(pentyloxy)carbonyl]amino | $CH_2$ | phenyl | $T^4\_1$ | $CH_3$ | 428 | $4.16^{[b]}$ |
| 61 | $A^{16}\_1$ | [(but-3-yn-1-yloxy)carbonyl]amino | $CH_2$ | phenyl | $T^4\_1$ | $CH_3$ | 410 | $3.11^{[b]}$ |
| 62 | $A^{16}\_1$ | cyclopropylethynyl | $CH_2$ | phenyl | $T^4\_1$ | $CH_3$ | 363 | $3.87^{[b]}$ |
| 63 | $A^{16}\_1$ | (tert-butoxycarbonyl)amino | $CH_2$ | phenyl | $T^4\_1$ | $CH_3$ | 414 | $3.69^{[b]}$ |
| 64 | $A^{16}\_1$ | (ethoxycarbonyl)amino | $CH_2$ | phenyl | $T^4\_1$ | $CH_3$ | 386 | $3^{[b]}$ |

Measurement of logP values was performed according EEC directive 79/831 Annex V.A8 by HPLC (High Performance Liquid Chromatography) on reversed phase columns with the following methods:
[a]Measurement was done at pH 2.3 with 0.1% phosphoric acid and acetonitrile as eluent.
[b]Measurement of LC-MS was done at pH 2.7 with 0.1% formic acid in water and with acetonitrile (contains 0.1% formic acid) as eluent with a linear gradient from 10% acetonitrle to 95% acetonitrile.
[c]Measurement with LC-MS was done at pH 7.8 with 0.001 molar ammonium hydrogen carbonate solution in water as eluent with a linear gradient from 10% acetonitrile to 95% acetonitrile.
Calibration was done with not branched alkan2-ones (with 3 to 16 carbon atoms) with known logP-values (measurement of logP values using retention times with linear interpolation between successive alkanones) . . . lambda-maX-values were determined using UV-spectra from 200 nm to 400 nm and the peak values of the chromatographic signals.
Double bond geometry: In the IUPAC-Names of the Examples 20, 21, 22, 23, 24, 25, 26, 27, 28 double bond geometry is labeled as Z. Double bond geometry of all other examples is not specified, but all potential mixtures of E, Z and the pure E- and Z-isomers are claimed.

Preparation of 6-[({[(3-fluorophenyl)(5-methyl-1,2,3-thiadiazol-4-yl)methylene]amino}oxy)methyl]-N-hexylpyridin-2-amine (Example 1)

Step 1: Preparation of tert-butyl hexyl[6-(hydroxymethyl)pyridin-2-yl]carbamate

To a stirred solution of tert-butyl[6-(hydroxymethyl)pyridin-2-yl]carbamate (3.79 g, 16.9 mmol) in DMF, cooled to 0° C. with a brine/ice bath, was added potassium tert-butoxide (126 mg, 1.07 mmol). The mixture was stirred 5 minutes at 0° C. then 1-bromo-2-cyclohexylethane (205 mg, 1.07 mmol) was added. After stirring at room temperature for 4 h, the reaction mixture was diluted with water (200 mL), extracted with ethyl acetate (150 mL). The organic layer was washed with water, dried (MgSO$_4$) and concentrated in vacuo. Purification on silica gel afforded tert-butyl hexyl[6-(hydroxymethyl)pyridin-2-yl]carbamate as a yellow oil [3.60 g, yield 69%; HPLC/MS: m/z=309 (M+H); log P$_{(HCOOH)}$=3.94].

Step 2: Preparation of tert-butyl (6-{[(1,3-dioxo-1,3-dihydro-2H-isoindol-2-yl)oxy]methyl}pyridin-2-yl)hexylcarbamate To a solution of tert-butyl hexyl[6-(hydroxymethyl)pyridin-2-yl]carbamate (2.52 g, 8.18 mmol) in acetonitrile (50 mL) was added N,N-diisopropylethylamine (1.59 g, 12.2 mmol). The solution was cooled to 0° C., then methanesulfonyl chloride (1.12 g, 9.81 mmol) was slowly added. After stirring at room temperature for 6 h, N-hydroxyphthalimide (1.46 g, 8.96 mmol), cesium carbonate (5.58 g, 17.1 mmol) and potassium iodide (135 mg, 0.81 mmol) were sequentially added, followed by acetonitrile (10 mL). The heterogenous mixture was stirred at room temperature for 20 h, then N-hydroxyphthalimide (0.33 g, 2.0 mmol) was added and the mixture was stirred at 50° C. for 7 h. The cooled reaction mixture was filtered and the filtrate was concentrated in vacuo. The oily residue was dissolved in ethyl acetate (200 mL), washed with water (100 mL), the organic layer was dried (MgSO$_4$) and concentrated in vacuo. Purification on silica gel afforded tert-butyl (6-{[(1,3-dioxo-1,3-dihydro-2H-isoindol-2-yl)oxy]methyl}pyridin-2-yl)hexylcarbamate as a yellow oil [2.107 g, yield 57%; HPLC/MS: m/z=454 (M+H); log P$_{(HCOOH)}$=5.48].

Step 3: Preparation of tert-butyl {6-[(aminooxy)methyl]pyridin-2-yl}hexylcarbamate To a solution of tert-butyl (6-{[(1,3-dioxo-1,3-dhydro-2H-isoindol-2-yl)oxy]methyl}pyridin-2-yl)hexylcarbamate (2.10 g, 4.63 mmol) in tetrahydrofuran (50 mL) was added hydrazine hydrate (464 mg, 9.28 mmol) dropwise. After stirring 7 h at room temperature, the reaction mixture was filtered, diluted with ethyl acetate, washed with water and the organic layer drid (MgSO$_4$) and concentrated in vacuo. Purification on silica gel afforded tert-butyl {6-[(aminooxy)methyl]pyridin-2-yl}hexylcarbamate as a colourless oil [1.29 g, yield 86%; HPLC/MS: m/z=324 (M+H); log P$_{(HCOOH)}$=3.42].

Step 4: Preparation of 6-[({[(3-fluorophenyl)(5-methyl-1,2,3-thiadiazol-4-yl)methylene]amino}oxy)methyl]-N-hexyl pyridin-2-amine A solution of (3-fluorophenyl)(5-methyl-1,2,3-thiadiazol-4-yl)methanone (61.8 mg, 0.27 mmol), tert-butyl {6-[(aminooxy)methyl]pyridin-2-yl}hexylcarbamate (98.9 mg, 0.30 mmol) and para-toluenesulfonic acid monohydrate (52.9 mg, 0.27 mmol) in 2-propanol was heated up to 160° C. by microwave irradiation for 2 h in a sealed tube. The cooled reaction mixture was diluted with dichloromethane (70 mL), washed with aq. sat. NaHCO$_3$ (50 mL), dried (MgSO$_4$) and concentrated in vacuo. Chromatography of the residue afforded the title compound as an orange oil [57 mg, yield 43%; HPLC/MS: m/z=428 (M+H); log P$_{(HCOOH)}$=3.06].

EXAMPLE 1

Preparation of 1-(3-chlorophenyl)-N-([2-(hex-1-yn-1-yl)-1,3-thiazol-4-yl]methoxy)-1-(5-methyl-1,2,3-thiadiazol-4-yl)methanimine (Example 6)

Step 1: Preparation of 2-[(2-amino-1,3-thiazol-4-yl)methoxy]-1H-isoindole-1,3(2H)-dione To a solution of 2-hydroxy-1H-isoindole-1,3(2H)-dione (4.13 g, 15.0 mmol) in acetonitrile (150 mL) were added 4-(chloromethyl)-1,3-thiazol-2-amine hydrochloride (50.1 g, 337 mmol), cesium carbonate (210 g, 643 mmol) and potassium iodide (2.54 g, 15.3 mmol). The heterogenous mixture was stirred at room temperature for 16 h. The reaction mixture was diluted with water, the insolubles were filtered off, rinsed with water and dried over night to afford 2-[(2-amino-1,3-thiazol-4-yl)methoxy]-1H-isoindole-1,3(2H)-dione as a colourless solid [36.0 g, yield 43%; HPLC/MS: m/z=276 (M+H); log P$_{(HCOOH)}$=0.74].

Step 2: Preparation of 2-[(2-bromo-1,3-thiazol-4-yl)methoxy]-1H-isoindole-1,3(2H)-dione To a suspension of 2-[(2-amino-1,3-thiazol-4-yl)methoxy]-1H-isoindole-1,3(2H)-dione (4.13 g, 15 mmol), NaBr (3.10 g, 30 mmol) and CuBr (2.15 g, 15 mmol) in acetonitrile (150 mL) at 40° C. under nitrogen atmosphere was added tert-butyl nitrite (2.32 mL, 19.5 mmol) dropwise over 30-40 min. After the addition was complete, heating was maintained towards an internal temp of 60-70° C., and the suspension was stirred at this temperature for 2 h. After cooling down, the mixture was diluted with water, and extracted with ethyl acetate. The combined organic layers (200 mL) were washed with aq HCl (1M, 50 mL), then with brine (50 mL) and dried (MgSO$_4$). After concentration on the rotary evaporator, the residue was purified on silica gel to afford 2-[(2-bromo-1,3-thiazol-4-yl)methoxy]-1H-isoindole-1,3(2H)-dione [1.50 g, yield 28%; HPLC/MS: m/z=339 (M+H); log P$_{(HCOOH)}$=2.39].

Step 3: Preparation of 2-{([2-(hex-1-yn-1-yl)-1,3-thiazol-4-yl]methoxy}-1H-isoindole-1,3(2H)-dione To a solution of 2-[(2-bromo-1,3-thiazol-4-yl)methoxy]-1H-isoindole-1,3(2H)-dione (23.1 g, 68.1 mmol) in dry tetrahydrofuran (300 mL) were added 1-hexyne (11.2 g, 136 mmol), triethylamine (13.8 g, 136 mmol). The reaction mixture was degassed by blowing a flow of Argon through it, then palladium tetrakis(triphenylphosphine) (3.94 g, 3.41 mmol) and copper iodide (1.30 g, 6.81 mmol) were added. After stirring at room temperature for 21 h under argon, the mixture was concentrated in vacuo, diluted with water (800 mL) and ethyl acetate (900 mL), the organic layer was washed with water, dried (MgSO$_4$) and concentrated in vacuo. Purification on silica gel afforded 2-{[2-(hex-1-yn-1-yl)-1,3-thiazol-4-yl]methoxy}-1H-isoindole-1,3(2H)-dione [13.6 g, yield 59%; HPLC/MS: m/z=341 (M+H); log P$_{(HCOOH)}$=3.78].

Step 4: Preparation of 4-[(aminooxy)methyl]-2-(hex-1-yn-1-yl)-1,3-thiazole

To a solution of 2-{[2-(hex-1-yn-1-yl)-1,3-thiazol-4-yl]methoxy}-1H-isoindole-1,3(2H)-dione (13.6 g, 40.1 mmol) in tetrahydrofuran (250 mL) was added methylhydrazine (3.69 g, 80.1 mmol) dropwise. After stirring 20 h at room temperature, the reaction mixture was concentrated in vacuo, diluted with ethyl acetate, washed with water and the organic layer drid (MgSO$_4$) and concentrated in vacuo. Purification on silica gel afforded 4-[(aminooxy)methyl]-2-(hex-1-yn-1-yl)-1,3-thiazole as a colourless oil [8.15 g, yield 94%; HPLC/MS: m/z=211 (M+H); log P$_{(HCOOH)}$=1.76].

Step 5: Preparation of 1-(3-chlorophenyl)-N-{([2-(hex-1-yn-1-yl)-1,3-thiazol-4-yl]methoxy}-1-(5-methyl-1,2,3-thiadiazol-4-yl)methanimine A solution of (3-chlorophenyl)(5-methyl-1,2,3-thiadiazol-4-yl)methanone (190 mg, 0.80 mmol), 4-[(aminooxy)methyl]-2-(hex-1-yn-1-yl)-1,3-thiazole (184 mg, 0.88 mmol) and para-toluenesulfonic acid monohydrate (151 mg, 0.80 mmol) in 2-propanol was stirred 4 h at 50° C. then 2 days at room temperature. The cooled reaction mixture was diluted with dichloromethane (70 mL), washed with aq. sat. NaHCO$_3$ (50 mL), dried (MgSO$_4$) and concentrated in vacuo. Chromatography of the residue afforded the title compound as an orange oil [175 mg, yield 51%; HPLC/MS: m/z=431 (M+H); log P$_{(HCOOH)}$=5.68].

EXAMPLE 2

Preparation of But-2-yn-1-yl {6-[({[(4-methyl-1,2,5-thiadiazol-3-yl)(phenyl)methylidene]amino}oxy)-methyl]pyridin-2-yl}carbamate (Example 25)

Step 1: Preparation of N-hydroxy-1-(4-methyl-1,2,5-thiadiazol-3-yl)-1-phenylmethanimine To a stirred solution of (4-Methyl-[1,2,5]thiadiazol-3-yl)-phenyl-methanone (20 g, 98 mmol) in dry pyridine (70 mL) was added hydroxylamine hydrochloride (17 g, 245 mmol). The reaction mixture was stirred at 70° C. for 3 h, then concentrated in vacuo and diluted with ethyl acetate (100 mL) and water (100 mL). The organic layer was washed with water (2×100 mL) and dried over MgSO$_4$. Evaporation of the solvent in vacuo afforded N-hydroxy-1-(4-methyl-1,2,5-thiadiazol-3-yl)-1-phenylmethanimine as an orange oil [24.3 g, yield 99.6%; HPLC/MS: m/z=220 (M+H); log P$_{(HCOOH)}$=2.26].

Step 2: Preparation of 2-{6-[({[(Z)-(4-methyl-1,2,5-thiadiazol-3-yl)(phenyl)methylene]amino}oxy)methyl]pyridin-2-yl}-1H-isoindole-1,3(2H)-dione To a stirred solution of N-hydroxy-1-(4-methyl-1,2,5-thiadiazol-3-yl)-1-phenylmethanimine (24.3 g, 111 mmol) in dry acetonitrile (600 mL) were added 2-[6-(bromomethyl)pyridin-2-yl]-1H-isoindole-1,3(2H)-dione (36.9 g, 116 mmol), cesium carbonate (37.9 g, 116 mmol) and potassium iodide (1.84 g, 11 mmol). The reaction mixture was stirred at room temperature for 14 h, then diluted with water (200 mL) and concentrated in vacuo. The residue was extracted with ethyl acetate (2×300 mL). The combined organic layers were combined and concentrated in vacuo to afford 2-{6-[({[(Z)-(4-methyl-1,2,5-thiadiazol-3-yl)(phenyl)methylene]amino}-oxy)methyl]pyridin-2-yl}-1H-isoindole-1,3(2H)-dione as a red oil [49 g, yield 82%; HPLC/MS: m/z=456 (M+H); log P$_{(HCOOH)}$=3.99].

Step 3: Preparation of 6-[({[(Z)-(4-methyl-1,2,5-thiadiazol-3-yl)(phenyl)methylene]amino}oxy)methyl]pyridin-2-amine To a stirred solution of 2-{6-[({[(Z)-(4-methyl-1,2,5-thiadiazol-3-yl)(phenyl)methylene]amino}-oxy)methyl]pyridin-2-yl}-1H-isoindole-1,3(2H)-dione (49 g, 91 mmol) in dry THF (800 mL) was added hydrazine hydrate (22.2 mL, 457 mmol). The reaction mixture was stirred at room temperature for 14 h, then insolubles were removed by filtration and washed with THF. The filtrates were combined and concentrated in vacuo. Purification of the residual oil on silica gel afforded 6-[({[(Z)-(4-methyl-1,2,5-thiadiazol-3-yl)(phenyl)methylene]amino}oxy)-methyl]pyridin-2-amine as a yellow oil [22.2 g, yield 75%; HPLC/MS: m/z=326 (M+H); log P$_{(HCOOH)}$=1.54].

Step 4: Preparation of but-2-yn-1-yl {6-[({[(4-methyl-1,2,5-thiadiazol-3-yl)(phenyl)methylidene]-amino}oxy)methyl]pyridin-2-yl}carbamate To a stirred solution of 6-[({[(Z)-(4-methyl-1,2,5-thiadiazol-3-yl)(phenyl)methylene]amino}oxy)methyl]pyridin-2-amine (100 mg, 0.31 mmol) in dry 1,4-dioxane (5 mL) were added pyridine (37 µL, 0.46 mmol) and but-2-yn-1-yl carbonochloridate (82 mg, 0.62 mmol). The reaction mixture was stirred at room temperature for 18 h, then diluted with DCM (10 mL) and water (10 mL), the organic layer was dried (MgSO$_4$) and concentrated in vacuo. Purification on silica gel afforded but-2-yn-1-yl {6-[({[(4-methyl-1,2,5-thiadiazol-3-yl)(phenyl)methylidene]-amino}oxy)methyl]pyridin-2-yl}carbamate as a colourless oil [120 mg, yield 93%; HPLC/MS: m/z=422 (M+H); log P$_{(HCOOH)}$=4.28].

EXAMPLE 3

Preparation of N-hexyl-6-[({[(4-methyl-1,2,5-thiadiazol-3-yl)(phenyl)methylidene]amino}oxy)methyl]-pyridin-2-amine (Example 31)

Step 1: Preparation of tert-butyl {6-[({[(4-methyl-1,2,5-thiadiazol-3-yl)(phenyl)methylene]-amino}oxy)methyl]pyridin-2-yl}carbamate To a stirred solution of 6-[({[(Z)-(4-methyl-1,2,5-thiadiazol-3-yl)(phenyl)methylene]amino}oxy)methyl]pyridin-2-amine (10 g, 31 mmol) in dry THF (150 mL) were added 4-dimethylaminopyridine (38 mg, 0.31 mmol) and di-tert-butyl dicarbonate (6.71 g, 31 mmol). The reaction mixture was stirred at room temperature for 2 days, then concentrated in vacuo. The residue was dissolved in ethyl acetate, washed with water, the organic layer was dried (MgSO$_4$) and concentrated in vacuo. Purification on silica gel afforded tert-butyl {6-[({[(4-methyl-1,2,5-thiadiazol-3-yl)(phenyl)methylene]-amino}oxy)methyl]pyridin-2-yl}carbamate as a yellow oil [2.72 g, yield 20%; HPLC/MS: m/z=426 (M+H); log P$_{(HCOOH)}$=4.97].

Step 2: Preparation of N-hexyl-6-[({[(4-methyl-1,2,5-thiadiazol-3-yl)(phenyl)methylene]amino}-oxy)methyl]pyridin-2-amine To a stirred solution of tert-butyl {6-[({[(4-methyl-1,2,5-thiadiazol-3-yl)(phenyl)methylene]-amino}oxy)methyl]pyridin-2-yl}carbamate (104 mg, 0.24 mmol) in dry DMF (5 mL) was added sodium hydride (60 wt.-% in mineral oil, 11 mg, 0.27 mmol). After stirring at room temperature for 15 min, 1-iodohexane (62 mg, 0.29 mmol) was added, and the mixture stirred at room temperature for 16 h. After dropwise addition of trifluoroacetic anhydride (1 mL, 13 mmol), the mixture was stirred at 50° C. for 8 h. The cooled reaction mixture was poured into sat. aq. NaHCO$_3$ (40 mL), extracted with ethyl acetate (2×30 mL), the organic layer was washed with water, dried (MgSO$_4$) and concentrated in vacuo. Purification on silica gel afforded N-hexyl-6-[({[(4-methyl-1,2,5-thiadiazol-3-yl)(phenyl)methylene]amino}-oxy)methyl]pyridin-2-amine as an orange oil [79 mg, yield 75%; HPLC/MS: m/z=410 (M+H); log P$_{(HCOOH)}$=3.11].

BIOLOGICAL EXAMPLES

Example A

Phytophthora Test (Tomato)/Preventive

Solvent: 49 parts by weight of N,N-Dimethylformamide
Emulsifier: 1 part by weight of Alkylarylpolyglycolether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Phytophthora infestans*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the control, while an efficacy of 100% means that no disease is observed.

In this test the following examples of table I according to the invention showed efficacy of 70% or even higher at a concentration of 100 ppm of active ingredient:

Example No. 20, 21, 22, 23, 24, 28, 26, 27, 30, 31, 32, 33, 34, 35, 36, 36, 37, 38, 50, 61, 62, 42, 43, 44 and 46.

The invention claimed is:
1. A compound of formula (I)

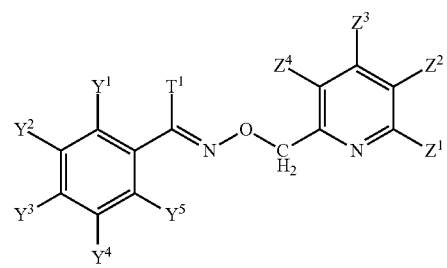

wherein:
T$^1$ is

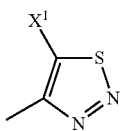

wherein:

$X^1$ is selected from the group consisting of a hydrogen atom, a halogen atom, a nitro group, a hydroxy group, a cyano group, an amino group, a sulfenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulfenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$—$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, and substituted or non-substituted (benzylideneamino)oxy;

$Z^1$ is selected from the group consisting of a nitro group, a hydroxy group, a formyl group, a substituted or non-substituted carbaldehyde O—($C_1$-$C_8$-alkyl)oxime, a formyloxy group, a carbamoyl group, a N-hydroxycarbamoyl group, a pentafluoro-$\lambda^6$-sulfenyl group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_3$-$C_8$-halogenocycloalkyl having 1 to 5 halogen atoms, a $C_2$-$C_8$- alkenyl, substituted or non-substituted C$_2$-C$_8$-alkynyl, substituted or non-substituted C$_1$-C$_8$-alkylamino, substituted or non-substituted di-C$_1$-C$_8$-alkylamino, substituted or non-substituted (C$_1$-C$_8$-alkoxycarbonyl)amino, substituted or non-substituted (C$_2$-C$_8$-alkenyloxycarbonyl)amino, substituted or non-substituted (C$_3$-C$_8$-alkynyloxycarbonyl)amino, substituted or non-substituted C$_2$-C$_8$-alkenyloxy, substituted or non-substituted C$_2$-C$_8$-halogenoalkenyloxy having 1 to 5 halogen atoms, substituted or non-substituted C$_3$-C$_8$-alkynyloxy, substituted or non-substituted C$_3$-C$_8$-halogenoalkynyloxy having 1 to 5 halogen atoms, substituted or non-substituted C$_1$-C$_8$-alkylcarbonyl, substituted or non-substituted N—(C$_1$-C$_8$-alkoxy)-C$_1$-C$_8$-alkanimidoyl, substituted or non-substituted N—(C$_1$-C$_8$-alkoxy)-C$_1$-C$_8$-halogenoalkanimidoyl having 1 to 5 halogen atoms, substituted or non-substituted C$_1$-C$_8$-alkylcarbamoyl, substituted or non-substituted di-C$_1$-C$_8$-alkylcarbamoyl, substituted or non-substituted N—C$_1$-C$_8$-alkyloxycarbamoyl, substituted or non-substituted C$_1$-C$_8$-alkoxycarbamoyl, substituted or non-substituted N—C$_1$-C$_8$-alkyl-C$_1$-C$_8$-alkoxycarbamoyl, substituted or non-substituted C$_1$-C$_8$-alkoxycarbonyl, substituted or non-substituted C$_1$-C$_8$-halogenoalkoxycarbonyl having 1 to 5 halogen atoms, substituted or non-substituted C$_1$-C$_8$-alkylcarbonyloxy, substituted or non-substituted C$_1$-C$_8$-halogenoalkylcarbonyloxy having 1 to 5 halogen atoms, substituted or non-substituted C$_1$-C$_8$-alkylaminocarbonyloxy, substituted or non-substituted di-C$_1$-C$_8$-alkylaminocarbonyloxy, substituted or non-substituted C$_1$-C$_8$-alkylcarbamothioyl, substituted or non-substituted di-C$_1$-C$_8$-alkylcarbamothioyl, substituted or non-substituted N—C$_1$-C$_8$-alkyloxycarbamothioyl, substituted or non-substituted C$_1$-C$_8$-alkoxycarbamothioyl, substituted or non-substituted N—C$_1$-C$_8$-alkyl-C$_1$-C$_8$-alkoxycarbamothioyl, substituted or non-substituted C$_1$-C$_8$-alkylthioylamino, substituted or non-substituted C$_1$-C$_8$-halogenoalkylthioylamino having 1 to 5 halogen atoms, substituted or non-substituted (C$_1$-C$_8$-alkoxythiocarbonyl)amino, substituted or non-substituted (C$_1$-C$_8$-alkylcarbamothioyl)-oxy, substituted or non-substituted (di-C$_1$-C$_8$-alkyl-carbamothioyl)-oxy, substituted or non-substituted C$_1$-C$_8$-alkylsulfinyl, substituted or non-substituted C$_1$-C$_8$-halogenoalkylsulfinyl having 1 to 5 halogen atoms, substituted or non-substituted C$_1$-C$_8$-alkylaminosulfamoyl, substituted or non-substituted di-C$_1$-C$_8$-alkylaminosulfamoyl, substituted or non-substituted (C$_1$-C$_6$-alkoxyimino)-C$_1$-C$_6$-alkyl, substituted or non-substituted (C$_1$-C$_6$-alkenyloxyimino)-C$_1$-C$_6$-alkyl, substituted or non-substituted (C$_1$-C$_6$-alkynyloxyimino)-C$_1$-C$_6$-alkyl, substituted or non-substituted (benzyloxyimino)-C$_1$-C$_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[C$_1$-C$_8$]-alkyl, substituted or non-substituted tri(C$_1$-C$_8$-alkyl)-silyloxy, substituted or non-substituted C$_1$-C$_8$-alkylsulfenylamino, substituted or non-substituted C$_1$-C$_8$-halogenoalkylsulfinylamino having 1 to 5 halogen atoms, substituted or non-substituted C$_1$-C$_8$-alkylsulfonylamino, substituted or non-substituted C$_1$-C$_8$-halogenoalkylsulfonylamino having 1 to 5 halogen atoms, substituted or non-substituted C$_1$-C$_8$-alkoxysulfonylamino, substituted or non-substituted C$_1$-C$_8$-halogenoxysulfonylamino having 1 to 5 halogen atoms, substituted or non-substituted tri(C$_1$-C$_8$-alkyl)-silyl, substituted or non-substituted (C$_1$-C$_6$-alkylideneamino)oxy, substituted or non-substituted (C$_1$-C$_6$-alkenylideneamino)oxy, substituted or non-substituted (C$_1$-C$_6$-alkynylideneamino)oxy, substituted or non-substituted (benzylideneamino)oxy, substituted or non-substituted [(arylcarbonyl)amino]-[C$_1$-C$_8$]-alkyl, substituted or non-substituted [{C$_1$-C$_8$-alkyl(C$_1$-C$_8$-alkylcarbonyl)amino}]-[C$_1$-C$_8$]-alkyl, substituted or non-substituted [{C$_1$-C$_8$-alkyl(arylcarbonyl)amino}]-C$_1$-C$_8$]-alkyl, and substituted or non-substituted [(C$_1$-C$_8$-alkylcarbonyl)amino]-[C$_1$-C$_8$]-alkyl;

$Z^2$, $Z^3$, $Z^4$, $Z^5$, $Z^6$ and $Z^7$ are independently selected from the group consisting of a nitro group, a hydroxy group, a formyl group, a substituted or non-substituted carbaldehyde O—(C$_1$-C$_8$-alkyl)oxime, a formyloxy group, a carbamoyl group, a N-hydroxycarbamoyl group, a pentafluoro-$\lambda^6$-sulfenyl group, substituted or non-substituted C$_1$-C$_8$-alkoxyamino group, substituted or non-substituted N—C$_1$-C$_8$-alkyl-(C$_1$-C$_8$-alkoxy)-amino group, substituted or non-substituted (C$_1$-C$_8$-alkylamino)-amino group, substituted or non-substituted N—C$_1$-C$_8$-alkyl-(C$_1$-C$_8$-alkylamino)-amino group, a substituted or non-substituted (hydroxyimino)-C$_1$-C$_6$-alkyl group, substituted or non-substituted tri (C$_1$-C$_8$-alkyl)silyl-C$_1$-C$_8$-alkyl, substituted or non-substituted C$_3$-C$_8$-cycloalkyl, substituted or non-substituted tri(C$_1$-C$_8$-alkyl)silyl-C$_3$-C$_8$-cycloalkyl, substituted or non-substituted C$_3$-C$_8$-halogenocycloalkyl having 1 to 5 halogen atoms, a C$_2$-C$_8$-alkenyl, substituted or non-substituted C$_2$-C$_8$-alkynyl, substituted or non-substituted C$_1$-C$_8$-alkylamino, substituted or non-substituted di-C$_1$-C$_8$-alkylamino, substituted or non-substituted (C$_1$-C$_8$-alkoxycarbonyl)amino, substituted or non-substituted (C$_2$-C$_8$-alkenyloxycarbonyl)amino, substituted or non-substituted (C$_3$-C$_8$-alkynyloxycarbonyl)amino, substituted or non-substituted C$_2$-C$_8$-alkenyloxy, substituted or non-substituted C$_2$-C$_8$-halogenoalkenyloxy having 1 to 5 halogen atoms, substituted or non-substituted C$_3$-C$_8$-alkynyloxy, substituted or non-substituted C$_3$-C$_8$-halogenoalkynyloxy having 1 to 5 halogen atoms, substituted or non-substituted C$_1$-C$_8$-alkylcarbonyl, substituted or non-substituted N—(C$_1$-C$_8$-alkoxy)-C$_1$-C$_8$-alkanimidoyl, substituted or non-substituted N—(C$_1$-C$_8$-alkoxy)-C$_1$-C$_8$-halogenoalkanimidoyl having 1 to 5 halogen atoms, substituted or non-substituted C$_1$-C$_8$-halogenoalkylcarbonyl having 1 to 5 halogen atoms, substituted or non-substituted C$_1$-C$_8$-alkylcarbamoyl, substituted or non-substituted di-C$_1$-C$_8$-alkylcarbamoyl, substituted or non-substituted N—C$_1$-C$_8$-alkyloxycarbamoyl, substituted or non-substituted C$_1$-C$_8$-alkoxycarbamoyl, substituted or non-substituted N—C$_1$-C$_8$-alkyl-C$_1$-C$_8$-alkoxycarbamoyl, substituted or non-substituted C$_1$-C$_8$-alkoxycarbonyl, substituted or non-substituted C$_1$-C$_8$-halogenoalkoxycarbonyl having 1 to 5 halogen atoms, substituted or non-substituted C$_1$-C$_8$-alkylcarbonyloxy, substituted or non-substituted C$_1$-C$_8$-halogenoalkylcarbonyloxy having 1 to 5 halogen atoms, substituted or non-substituted C$_1$-C$_8$-alkylaminocarbonyloxy, substituted or non-substituted di-C$_1$-C$_8$-alkylaminocarbonyloxy, substituted or non-substituted C$_1$-C$_8$-alkylcarbamothioyl, substituted or non-substituted di-C$_1$-C$_8$-alkylcarbamothioyl, substituted or non-substituted N—C$_1$-C$_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkoxythiocarbonyl)amino, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[$C_1$-$C_8$]-alkyl, substituted or non-substituted tri($C_1$-$C_8$)-silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy, substituted or non-substituted [(arylcarbonyl)amino]-[$C_1$-$C_8$]-alkyl, substituted or non-substituted [{$C_1$-$C_8$-alkyl($C_1$-$C_8$-alkylcarbonyl)amino}]-[$C_1$-$C_8$]-alkyl, substituted or non-substituted [{$C_1$-$C_8$-alkyl(arylcarbonyl)amino}]-[$C_1$-$C_8$]-alkyl, and substituted or non-substituted [($C_1$-$C_8$-alkylcarbonyl)amino]-[$C_1$-$C_8$]-alkyl;

$Y^1$ through $Y^5$ are independently selected from the group consisting of a hydrogen atom, a nitro group, a hydroxy group, a cyano group, an amino group, a sulfenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulfenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, and substituted or non-substituted (benzylideneamino)oxy; as well as any salt, N-oxide, (E) and/or (Z) isomer, or any mixture thereof.

2. The compound of claim 1 wherein said compound is

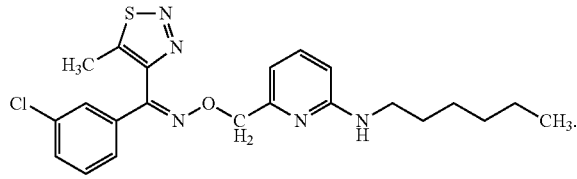 [SMILES: CCCCCCNc1cccc(CO/N=C(/c2cccc(Cl)c2)c2nnsc2C)n1]

3. A method for controlling the phytopathogenic fungi or damaging insects of plants, crops or seeds comprising applying an agronomically effective and substantially non-phytotoxic quantity of the compound of claim 2 as seed treatment, foliar application, stem application, drench or drip application or chemigation to the seed, the plant or to the fruit of the plant or to soil or to inert substrate, Pumice, Pyroclastic materials/tuff, synthetic organic substrates organic substrates or to a liquid substrate wherein the plant is growing or wherein it is desired to grow.

4. The compound of claim 1 wherein $X^1$ is selected from the group consisting of a hydrogen atom, a halogen atom, a cyano group, an amino group, a sulfenyl group, a pentafluoro-$\lambda^6$-sulfenyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted phenoxy, substituted or non-substituted phenylsulfenyl, substituted or non-substituted aryl, substituted or non-substituted aryl-[$C_1$-$C_8$]-alkyl, substituted or non-substituted tri($C_1$-$C_8$-alkyl)-silyloxy, and substituted or non-substituted tri($C_1$-$C_8$-alkyl)-silyl.

5. The compound of claim 4 wherein $X^1$ is selected from the group consisting of a hydrogen atom, a halogen atom, methyl, isopropyl, isobutyl, tertbutyl, trifluoromethyl, difluoromethyl, allyl, ethynyl, propargyl, cyclopropyl, benzyl, phenethyl, methoxy, trifluoromethoxy, acetyl, trifluoroacetyl and cyano.

6. The compound of claim 1 wherein $Z^1$ is selected from the group consisting of substituted or non-substituted $C_1$-$C_8$-alkoxyamino, substituted or non-substituted N—$C_1$-$C_8$-alkyl-($C_1$-$C_8$-alkoxy)-amino, substituted or non-substituted $C_3$-$C_8$-cycloalkyl, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkylcarbonyl, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted ($C_1$-$C_8$-alkoxycarbonyl)amino, substituted or non-substituted ($C_2$-$C_8$-alkenyloxycarbonyl)amino, substituted or non-substituted ($C_3$-$C_8$-alkynyloxycarbonyl)amino, substituted or non-substituted ($C_1$-$C_8$-alkoxythiocarbonyl)amino, substituted or non-substituted $C_1$-$C_8$-alkylthioylamino, substituted or non-substituted benzylamino, substituted or non-substituted phenylamino, and substituted or non-substituted aryl-[$C_1$-$C_8$]-alkyl.

7. The compound of claim 6 wherein $Z^1$ is selected from the group consisting of substituted or non-substituted $C_1$-$C_8$-alkoxyamino, substituted or non-substituted $C_3$-$C_8$-cycloalkyl, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted ($C_1$-$C_8$-alkoxycarbonyl)amino, substituted or non-substituted ($C_2$-$C_8$-alkenyloxycarbonyl)amino, substituted or non-substituted ($C_3$-$C_8$-alkynyloxycarbonyl)amino, substituted or non-substituted ($C_1$-$C_8$-alkoxythiocarbonyl)amino, substituted or non-substituted $C_1$-$C_8$-alkylthioylamino, substituted or non-substituted benzylamino, substituted or non-substituted phenylamino, and substituted or non-substituted aryl-[$C_1$-$C_8$]-alkyl.

8. The compound of claim 1 wherein $Z^2$ through $Z^4$ are independently selected from the group consisting of substituted or non-substituted $C_3$-$C_8$-cycloalkyl, a $C_2$-$C_8$-alkenyl, substituted or non-substituted $C_2$-$C_8$-alkynyl, substituted or non-substituted phenoxy, substituted or non-substituted aryl, and substituted or non-substituted aryl-[$C_1$-$C_8$]-alkyl.

9. The compound of claim 8 wherein $Z^2$ through $Z^4$ are independently selected from the group consisting of allyl, ethynyl, propargyl, and cyclopropyl.

10. The compound of claim 1 wherein $Y^1$ through $Y^5$ are independently selected from the group consisting of a hydrogen atom, a halogen atom, a cyano group, an amino group, a sulfenyl group, a pentafluoro-$\lambda^6$-sulfenyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted phenoxy, substituted or non-substituted phenylsulfenyl, substituted or non-substituted aryl, substituted or non-substituted aryl-[$C_1$-$C_8$]-alkyl, substituted or non-substituted tri($C_1$-$C_8$-alkyl)-silyloxy, and substituted or non-substituted tri($C_1$-$C_8$-alkyl)-silyl.

11. The compound of claim 10 wherein $Y^1$ through $Y^5$ are independently selected from the group consisting of a hydrogen atom, a halogen atom, methyl, isopropyl, isobutyl, tert-butyl, trifluoromethyl, difluoromethyl, allyl, ethynyl, propargyl, cyclopropyl, methoxy, trifluoromethoxy and cyano.

12. A method for controlling the phytopathogenic fungi or damaging insects of plants, crops or seeds comprising applying an agronomically effective and substantially non-phytotoxic quantity of the compound of claim 1 as seed treatment, foliar application, stem application, drench or drip application or chemigation to the seed, the plant or to the fruit of the plant or to soil or to inert substrate, Pumice, Pyroclastic materials/tuff, synthetic organic substrates organic substrates or to a liquid substrate wherein the plant is growing or wherein it is desired to grow.

* * * * *

UNITED STATES PATENT AND TRADEMARK OFFICE
CERTIFICATE OF CORRECTION

PATENT NO. : 8,580,799 B2  Page 1 of 1
APPLICATION NO. : 13/133916
DATED : November 12, 2013
INVENTOR(S) : Beier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 62 days.

Signed and Sealed this
Twenty-second Day of September, 2015

Michelle K. Lee
*Director of the United States Patent and Trademark Office*